(12) United States Patent
Vaillant et al.

(10) Patent No.: US 8,716,259 B2
(45) Date of Patent: May 6, 2014

(54) OLIGONUCLEOTIDE CHELATE COMPLEXES

(71) Applicant: Replicor Inc., Montréal (CA)

(72) Inventors: Andrew Vaillant, Roxboro (CA); Michel Bazinet, Montréal (CA)

(73) Assignee: Replicor Inc., Montreal (CA)

( * ) Notice: Subject to any disclaimer, the term of this patent is extended or adjusted under 35 U.S.C. 154(b) by 0 days.

(21) Appl. No.: 13/905,318

(22) Filed: May 30, 2013

(65) Prior Publication Data

US 2013/0296410 A1    Nov. 7, 2013

Related U.S. Application Data

(62) Division of application No. 13/212,306, filed on Aug. 18, 2011, now Pat. No. 8,513,211.

(60) Provisional application No. 61/375,257, filed on Aug. 20, 2010.

(51) Int. Cl.
  *A61K 31/712* (2006.01)
  *A61K 31/7125* (2006.01)
  *A61K 31/7115* (2006.01)
  *C07H 21/04* (2006.01)
  *C12Q 1/68* (2006.01)

(52) U.S. Cl.
  USPC ............ 514/44; 424/1.53; 424/406; 424/722; 435/6.1; 435/91.1; 435/91.31; 435/465

(58) Field of Classification Search
  USPC ......... 424/1.53, 406, 722; 435/6.1, 465, 91.1, 435/91.3; 514/1, 44; 536/23.1, 24.5
  See application file for complete search history.

(56) References Cited

U.S. PATENT DOCUMENTS

| 6,011,143 A | 1/2000 | Shionoya et al. |
| 2006/0074041 A1 | 4/2006 | Johnston et al. |
| 2006/0293510 A1 | 12/2006 | Shionoya et al. |
| 2007/0105116 A1 | 5/2007 | Shionoya et al. |

FOREIGN PATENT DOCUMENTS

| WO | 2007005626 | 1/2007 |
| WO | 2009065181 | 5/2009 |

OTHER PUBLICATIONS

Levin et al., 1998, "Toxicity of Oligodeoxynucleotide Therapeutic Agents". Chapter 5 in Antisense Research and Application. Handbook of Experimental Pharmacology 131: 169-215.
Tamm et al., 2001, "Antisense therapy in oncology: new hope for an old idea?". Lancet, 358: 489-97.
Van de Donk et al., 2004, "G3139, a BCL-2 antisense oligodeoxynucleotide, induced clinical responses in VAD refractory myeloma". Leukemia, 18: 1078-1084.
Nemunaitis et al., 1999, "Phase I Evaluation of ISIS 3521, an Antisense Oligodeoxynucleotide to Protein Kinase C-Alpha, in Patients With Advanced Cancer". J. Clin. Oncol., 17: 3586-3595.
Sewell et al., 2002, "Phase I Trial of ISIS 104838, a 2'-Methoxyethyl Modified Antisense Oligonucleotide Targeting Tumor Necrosis Factor-$\alpha$". J. Pharm. Exp. Therap., 303: 1334-1343.
Lippi and Favaloro, 2011, "Antisense therapy in the treatment of hypercholesterolemia". Eur. J. Int. Med, 22: 541-546.
IPRP from corresponding PCT application, Nov. 14, 2012.
International Search Report of corresponding International application No. PCT/CA2011/000956 dated Dec. 1, 2011.
Zimmer et al., CD studies on the conformation of ligonucleotides complexed with divalent metal ions . . . , Nucleic Acids Research, Oct. 1976, vol. 3, No. 10, pp. 2757-2770.
Beck et al., Electrospray ionisation mass spectrometry of ruthenium and palldium complexes with oligonucleotides, Eur. Mass Spectrom., 1999, No. 5, pp. 489-500.
Fischer et al., Oligonucleotides are potent antioxidants acting mainly as metal-ion chelators, Nucleic Acids Symposium, Sep. 8, 2008, Series No. 52, pp. 485-486.
Zobel et al., Oligonucleotides are potent antioxidants acting primarily through metal ion chelation, J Biol Inorg Chem, 2010, No. 15, 601-620.

*Primary Examiner* — Jane Zara
(74) *Attorney, Agent, or Firm* — Norton Rose Fulbright Canada

(57) ABSTRACT

The present disclosure describes the broadly active chelation of diverse divalent 2+ metal cations by any oligonucleotide (ON), regardless of size or modification. This chelation effect is specific to cations which are divalent (or of higher valency) and results in the formation of oligonucleotide chelate complexes which do not behave like salts. It is described herein a novel composition of an ON chelate complex prepared using any ON and a divalent metal cation and methods for the suppression of anti-coagulation and or subcutaneous injection site reactions and or improved tolerability with oligonucleotides by the use of ON chelate complexes during oligonucleotide administration.

14 Claims, 30 Drawing Sheets

```
                           SEQUENCE LISTING

<160> NUMBER OF SEQ ID NOS: 14

<210> SEQ ID NO 1
    <211> LENGTH: 40
    <212> TYPE: DNA
    <213> ORGANISM: Artificial Sequence
    <220> FEATURE:
    <223> OTHER INFORMATION: REP 2028, full phosphorothioate

<400> SEQUENCE: 1
gggggggggg gggggggggg gggggggggg gggggggggg                              40

<210> SEQ ID NO 2
    <211> LENGTH: 40
    <212> TYPE: DNA
    <213> ORGANISM: Artificial Sequence
    <220> FEATURE:
    <223> OTHER INFORMATION: REP 2029, full phosphorothioate

<400> SEQUENCE: 2
aaaaaaaaaa aaaaaaaaaa aaaaaaaaaa aaaaaaaaaa                              40

<210> SEQ ID NO 3
    <211> LENGTH: 40
    <212> TYPE: DNA
    <213> ORGANISM: Artificial Sequence
    <220> FEATURE:
    <223> OTHER INFORMATION: REP 2030, full phosphorothioate

<400> SEQUENCE: 3
tttttttttt tttttttttt tttttttttt tttttttttt                              40

<210> SEQ ID NO 4
    <211> LENGTH: 40
    <212> TYPE: DNA
    <213> ORGANISM: Artificial Sequence
    <220> FEATURE:
    <223> OTHER INFORMATION: REP 2031, full phosphorothioate

<400> SEQUENCE: 4
cccccccccc cccccccccc cccccccccc cccccccccc                              40

<210> SEQ ID NO 5
    <211> LENGTH: 40
    <212> TYPE: DNA
    <213> ORGANISM: Artificial Sequence
    <220> FEATURE:
```

-continued

```
<223> OTHER INFORMATION: REP 2033, full phosphorothioate

<400> SEQUENCE: 5
tgtgtgtgtg tgtgtgtgtg tgtgtgtgtg tgtgtgtgtg                              40

<210> SEQ ID NO 6
<211> LENGTH: 40
<212> TYPE: DNA
<213> ORGANISM: Artificial Sequence
<220> FEATURE:
<223> OTHER INFORMATION: REP 2055, full phosphorothioate

<400> SEQUENCE: 6
acacacacac acacacacac acacacacac acacacacac                              40

<210> SEQ ID NO 7
<211> LENGTH: 40
<212> TYPE: DNA
<213> ORGANISM: Artificial Sequence
<220> FEATURE:
<223> OTHER INFORMATION: REP 2056, full phosphorothioate

<400> SEQUENCE: 7
tctctctctc tctctctctc tctctctctc tctctctctc                              40

<210> SEQ ID NO 8
<211> LENGTH: 40
<212> TYPE: DNA
<213> ORGANISM: Artificial Sequence
<220> FEATURE:
<223> OTHER INFORMATION: REP 2057, full phosphorothioate

<400> SEQUENCE: 8
agagagagag agagagagag agagagagag agagagagag                              40

<210> SEQ ID NO 9
<211> LENGTH: 20
<212> TYPE: DNA
<213> ORGANISM: Artificial Sequence
<220> FEATURE:
<223> OTHER INFORMATION: REP 2126, full phosphorothioate

<400> SEQUENCE: 9
cccccccccc cccccccccc                                                    20

<210> SEQ ID NO 10
<211> LENGTH: 30
<212> TYPE: DNA
<213> ORGANISM: Artificial Sequence
<220> FEATURE:
<223> OTHER INFORMATION: REP 2127, full phosphorothioate

<400> SEQUENCE: 10
cccccccccc cccccccccc cccccccccc                                         30

<210> SEQ ID NO 11
<211> LENGTH: 50
<212> TYPE: DNA
<213> ORGANISM: Artificial Sequence
<220> FEATURE:
<223> OTHER INFORMATION: REP 2128, full phosphorothioate

<400> SEQUENCE: 11
cccccccccc cccccccccc cccccccccc cccccccccc cccccccccc                   50

<210> SEQ ID NO 12
```

-continued

```
<211> LENGTH: 60
<212> TYPE: DNA
<213> ORGANISM: Artificial Sequence
<220> FEATURE:
<223> OTHER INFORMATION: REP 2129, full phosphorothioate

<400> SEQUENCE: 12
cccccccccc cccccccccc cccccccccc cccccccccc cccccccccc cccccccccc      60

<210> SEQ ID NO 13
<211> LENGTH: 40
<212> TYPE: DNA
<213> ORGANISM: Artificial Sequence
<220> FEATURE:
<223> OTHER INFORMATION: REP 2139, full phosphorothioate, full 2' O
      methyl ribose, C = 5' methylcytidine

<400> SEQUENCE: 13
acacacacac acacacacac acacacacac acacacacac      40

<210> SEQ ID NO 14
<211> LENGTH: 40
<212> TYPE: DNA
<213> ORGANISM: Artificial Sequence
<220> FEATURE:
<223> OTHER INFORMATION: REP 2138; full  2' O methyl ribose

<400> SEQUENCE: 14
cccccccccc cccccccccc cccccccccc cccccccccc      40
```

OLIGONUCLEOTIDE CHELATE COMPLEXES

CROSS REFERENCE TO RELATED APPLICATION

This application is a divisional application of U.S. application Ser. No. 13/212,306 filed Aug. 18, 2011, which claims priority from of U.S. Provisional Application Ser. No. 61/375,257, filed Aug. 20, 2010, the specification of which is hereby incorporated by reference. A sequence listing in electronic form is also part of the specification.

TECHNICAL FIELD

The present invention relates to oligonucleotide chelate complexes, compositions thereof and methods for the formulation of oligonucleotides (ONs) as chelate complexes and the use of these ON chelate complexes for ON administration

BACKGROUND ART

Salts are ionic compounds which result from the interaction (neutralization) of an acid and a base. Salts are composed of cations and anions which interact so that an electrically neutral state is maintained. Anions can be inorganic (such as $Cl^-$) or organic such as acetate ($CH_3COO^-$). Aqueous solutions containing dissolved salts (electrolytes) are able to conduct electricity due to the dissociated state of the anion and cation pairs in an aqueous environment. Oligonucleotides are polyanions and have been previously thought to only behave as salts where their cation counterparts exist in solution in a dissociated state.

The administration of ONs to human patients has typically been accompanied by several generalized side effects not related to the nucleotide sequence present. These include anti-coagulation (elevation of pro-thrombin time or PTT time) of the blood (Kandmimlla et al., 1998, Bioorgan. Med. Chem. Let., 8: 2103; Sheeban et al., Blood, 1998, 92: 1617; Nicklin et al., 1197, Nucleosides & Nucleotides, 16: 1145; Kwoh, 2008, Antisense Drug Tech. 2nd Ed., p374) and injection site reactions or ISRs (induration, inflammation, tenderness and pain) with subcutaneous administration (Webb et al., 1997, Lancet, 349: 9059; Schrieber et al., 2001, Gastroenterol., 120: 1339; Seawell et al., 2002, J. Pharmacol. Exp. Therap., 303: 1334; Kwoh, 2008, Antisense Drug Tech. 2nd Ed., p383; Raal et al., 2010, Lancet, 375: 998). The anti-coagulation effects are thought to be mediated by non-sequence specific interaction with proteins of the coagulation cascade. As ONs have been shown to possess immunostimulatory properties (via Toll-like receptor or TLR-mediated cytokine induction), ISR's have typically been attributed to the requirement for high concentration ON administration in a small volume (typically 1 cc) for subcutaneous (SC) injection, which is thought to lead to local inflammation at the injection site.

With the advent of nucleic-acid based therapy in recent years, the increased numbers of ON-based compounds in clinical development has increased. Historically most ON dosing regimens have employed multiple doses in a week or single weekly doses which must be given parenterally due to the poor oral bioavailability of ONs. Since intravenous infusion of ONs is typically dose and rate limited by reactivity (fever, shivering, weakness) and would be logistically demanding in a chronic dosing scenario, more recent clinical application of ONs have used the subcutaneous (SC) route of administration. This leads to minimal systemic dosing side effects but is typically accompanied by injection site reactions of varying degrees of severity (as described above) which also limit the dosing achievable by this route of administration.

It would therefore be useful and desirable to be provided with an ON formulation which would mitigate reactivity during either IV or SC routes of administration. Furthermore, while the anti-coagulation effects of ON administration are considered minimal, it would also be useful to neutralize this side effect of ONs to provide for a greater margin of safety in human and non-human subjects.

There is thus a need to be provided with an improved ON formulation.

SUMMARY

In accordance with the present description there is now provided an oligonucleotide chelate complex comprising two or more oligonucleotides linked by a multivalent cation.

It is further provided an oligonucleotide formulation for subcutaneous administration, the oligonucleotide formulation comprising the oligonucleotide chelate complex as described herein.

It is also disclosed a pharmaceutical composition comprising the oligonucleotide chelate complex or the oligonucleotides formulation described herein and a carrier.

It is further disclosed a method of reducing liver or kidney dysfunction associated with oligonucleotide administration to a subject comprising the step of administering the oligonucleotide to the subject as a chelate complex as described herein, an oligonucleotide formulation as disclosed herein, or a pharmaceutical composition as disclosed herein.

It is disclosed herein methods for the suppression, inhibition or reduction of blood anti-coagulation by ONs by administering the ON as a calcium chelate complex or other appropriate ON metal chelate complexes, oligonucleotide formulation described herein, or a pharmaceutical composition described herein.

It is also disclosed herein methods for the improvement of the tolerability of any ON administered by IV infusion by preparing the ON as a calcium chelate complex or other appropriate ON metal chelate complexes, oligonucleotide formulation described herein, or a pharmaceutical composition described herein.

It is disclosed herein methods for the suppression or reducing of injection site reactions with administering the ON as a calcium chelate complex or other appropriate ON metal chelate complexes, oligonucleotide formulation described herein, or a pharmaceutical composition described herein. Particularly, the ON is subcutaneously administered.

It is disclosed herein methods for the suppression of metal chelation with any ON administered by any route by providing the ON as a calcium chelate complex or other appropriate ON metal chelate complexes, oligonucleotide formulation described herein, or a pharmaceutical composition described herein.

It is disclosed herein methods for the reduction of the serum ½ life of any ON by the administration of the ON as a calcium chelate complex or other appropriate ON metal chelate complexes, oligonucleotide formulation described herein, or a pharmaceutical composition described herein.

It is disclosed herein methods for the reduction of serum protein interactions with any ON by the administration of the ON as a calcium chelate complex or other appropriate metal chelate complexes, an oligonucleotide formulation as described herein, or a pharmaceutical composition as described herein. Particularly, the oligonucleotide chelate complex, formulation or composition are administered by IV infusion to a subject.

It is also disclosed herein an oligonucleotide formulation wherein a source of divalent metal cation from any of the following list is provided with the oligonucleotide as an ON chelate complex at the time of oligonucleotide use: calcium, magnesium, cobalt, iron, manganese, barium, nickel, copper, and/or zinc. It is thus described herein an oligonucleotide formulation comprising calcium; an oligonucleotide formulation comprising magnesium; an oligonucleotide formulation comprising cobalt; an oligonucleotide formulation comprising iron (2+); an oligonucleotide formulation comprising manganese; an oligonucleotide formulation comprising copper; an oligonucleotide formulation comprising zinc.

It is disclosed herein methods for the manufacture of ON metal chelate complexes using any of the following metal cations, individually or in combination: calcium, magnesium, cobalt, iron, manganese, barium, nickel, copper, and/or zinc.

It is also disclosed a method for the preparation of the oligonucleotide chelate complex as described herein, the oligonucleotide formulation described herein, or pharmaceutical composition described herein, the method comprising dissolving any oligonucleotide sodium salt in an pharmaceutically acceptable aqueous excipient, and gradually adding a divalent metal salt solution to the dissolved oligonucleotide such that the oligonucleotide chelate complex remains soluble.

It is disclosed herein a method for chelating the following divalent metal cations within a subject using a oligonucleotide sodium salt: calcium, magnesium, cobalt, iron, manganese, barium, nickel, copper, zinc, cadmium, mercury, lead, beryllium, strontium, radium, and/or any other metal, transition metal, post-transition metal, lanthanide or actinide element capable of existing in the 2+ or 3+ charge state.

It is also disclosed herein a method of improving the stability of any ON in solution by preparing the ON as a calcium chelate complex or other appropriate ON metal chelate complex, oligonucleotide formulation described herein, or a pharmaceutical composition described herein. Particularly, it is disclosed a method of stabilizing an oligonucleotide in an aqueous solution.

It is encompassed herein that the multivalent cation is a divalent cation.

It is encompassed herein that the divalent cation is an alkali earth metal with a 2+ charge state.

It is encompassed herein that the divalent cation is a transition or post-transition metal with a 2+ charge state.

It is encompassed herein that the divalent cation is a lanthanide metal with a 2+ charge state.

It is encompassed herein that the divalent cation is an actinide metal with a 2+ charge state.

The divalent cation can be, individually or in combination: calcium, magnesium, cobalt, iron, manganese, barium, nickel, copper, and/or zinc.

Particularly, the chelate complex described herein can comprise two or more different divalent metal cations.

In a further embodiment, the chelate complex comprises at least one double stranded oligonucleotide.

In another embodiment, the chelate complex comprises at least one oligonucleotide with one phosphorothioate linkage.

The chelate complex can also comprise at least one fully phosphorothioated oligonucleotide.

The chelate complex can also comprise at least one oligonucleotide with one 2' modified ribose.

The chelate complex can also comprise at least one oligonucleotide which has each ribose 2' O-methylated.

In an embodiment, the chelate complex or formulation is adapted for subcutaneous administration; is adapted for at least of the following routes of administration: intraocular, oral ingestion, enteric, inhalation, cutaneous injection, intramuscular injection, intraperitoneal injection, intrathecal injection, intrathecal infusion, intratracheal, intravenous injection, intravenous infusion and topically. Particularly, inhalation administration can be an aerosol.

It is further encompassed that the oligonucleotide consists of SEQ ID NOs: 3 to 14.

It is further encompassed that the dissolved oligonucleotide concentration is 0.01-100 mg/ml prior to the metal salt addition.

Particularly, the ratio of metal salt added to the dissolved oligonucleotide can be 0.1-40 mg of divalent salt per 100 mg of oligonucleotide.

It is further encompassed that final oligonucleotide concentration is 0.1-100 mg/ml.

In a further embodiment, the metal salt is at least one of a chloride salt, a gluconate salt, a citrate salt, a lactate salt, a malate salt, an aspartate salt, a fumarate salt, an ascorbate salt, a benzoate salt, an erythorbate salt and a propionate salt.

In another embodiment, the metal salt solution contains at least one of calcium, magnesium, cobalt, iron (2+), manganese, copper and/or zinc.

It is also encompassed a chelate complex being a calcium chelate complex; a magnesium chelate complex; or a mixed magnesium/calcium chelate complex.

It is also provided the use of a multivalent cation as described herein in the manufacture of an oligonucleotide chelate complex.

It is additionally provided the use of the oligonucleotide chelate complex as described herein, the oligonucleotide formulation described herein, or pharmaceutical composition described herein for suppressing or reducing the anti-coagulation effect of the oligonucleotide administration to a subject.

It is provided the use of the oligonucleotide chelate complex as described herein, the oligonucleotide formulation described herein, or pharmaceutical composition described herein for suppressing or reducing subcutaneous injection site reactions in a subject of said subcutaneously administered oligonucleotide.

It is also provided the use of the oligonucleotide chelate complex as described herein, the oligonucleotide formulation described herein, or pharmaceutical composition described herein for improving the tolerability of the oligonucleotide in a subject when administered by IV infusion.

It is also provided the use of the oligonucleotide chelate complex as described herein, the oligonucleotide formulation described herein, or pharmaceutical composition described herein for reducing serum protein interaction of an oligonucleotide when administered by IV infusion to a subject.

It is further provided the use of the oligonucleotide chelate complex as described herein, the oligonucleotide formulation described herein, or pharmaceutical composition described herein for reducing the serum ½ life of the oligonucleotide in a subject.

It is also provided the use of the oligonucleotide chelate complex as described herein, the oligonucleotide formulation described herein, or pharmaceutical composition described herein for reducing liver or kidney dysfunction associated with the oligonucleotide administration in a subject.

It is also provided the use of the oligonucleotide chelate complex as described herein, the oligonucleotide formulation described herein, or pharmaceutical composition described herein for the stabilization of an oligonucleotide in an aqueous solution.

The expression "anti-coagulation" is intended to mean the inhibition of normal blood coagulation or clot formation.

The expression "chelation" is intended to mean the sequestration or removal from free solution reaction a counter-ion (negative or positive) by another molecule capable of binding to the counter-ion, forming a chelated complex.

The expression "divalent metal cation" is intended to mean any metal cation which can naturally exist in the 2+ charge state and includes alkaline earth metals (group 2 elements according to IUPAC nomenclature), transition metals, post-transition metals, metalloids or lanthanoids.

The expression "trivalent metal cation" is intended to mean any metal cation which naturally exists in the 3+ charge state and includes transition metals, post-transition metals, metalloids, lanthanoids or actinoids.

BRIEF DESCRIPTION OF THE DRAWINGS

Reference will now be made to the accompanying drawings:

FIG. 1 illustrates the common physiochemical features of ONs.

FIG. 17 shows the formation of ON chelate complexes with calcium chloride or calcium sulfate as measured by fluorescence polarization.

FIG. 18 shows the formation of ON chelate complexes with calcium chloride or calcium sulfate as measured by fluorescence polarization.

FIG. 19 shows the formation of ON chelate complexes with calcium chloride or calcium sulfate as measured by fluorescence polarization.

FIG. 20 shows the formation of ON chelate complexes with calcium chloride or calcium sulfate as measured by fluorescence polarization.

FIG. 21 shows the formation of ON chelate complexes with magnesium chloride or magnesium sulfate as measured by fluorescence polarization.

FIG. 22 shows the formation of ON chelate complexes with magnesium chloride or magnesium sulfate as measured by fluorescence polarization.

FIG. 23 shows the formation of ON chelate complexes with magnesium chloride or magnesium sulfate as measured by fluorescence polarization.

FIG. 24 shows the formation of ON chelate complexes with magnesium chloride or magnesium sulfate as measured by fluorescence polarization.

DETAILED DESCRIPTION

It is provided herein a demonstration that ONs chelate diverse divalent metal cations including calcium, magnesium, cobalt, iron, manganese, barium, nickel, copper, zinc, cadmium, mercury and lead. It is further demonstrated that chelation of these divalent cations results in the formation of ON chelate complexes comprised of two or more ONs linked via metal cations and occur as exemplified, but not limited to, ONs between 6 and 80 nucleotides in length, and in the presence of phosphodiester or phosphorothioate oligonucleotides. Chelation also occurs with oligonucleotides containing 2' modifications at the ribose or not. Moreover, the chelation of the metal cations is not dependent on the sequence of nucleotides present but instead relies on the physiochemical features common to all oligonucleotides (see FIG. 14A).

Figure 14:
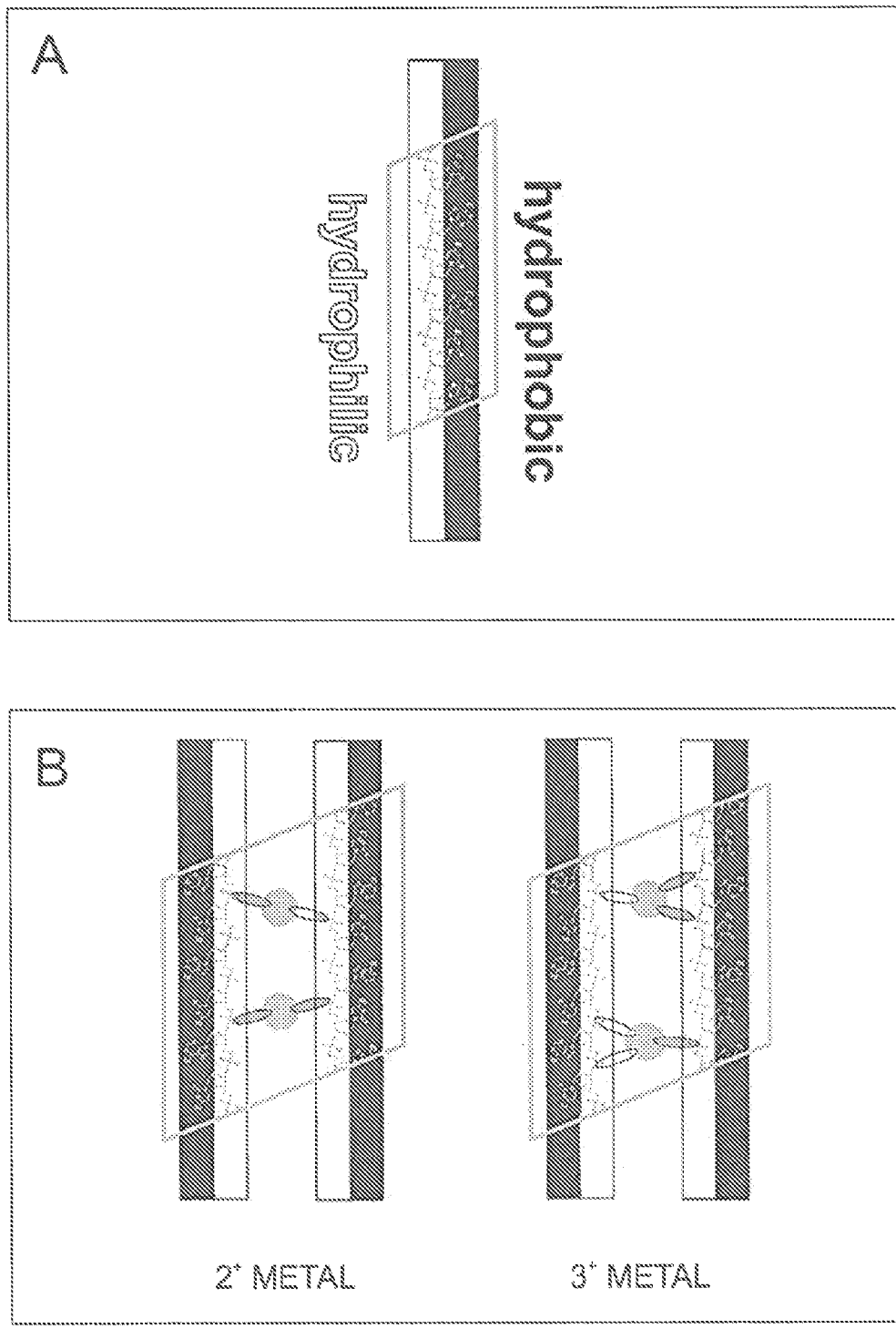
FIG. 14A illustrates the general chemical features of ONs which are not dependent on ON sequence. Regardless of sequence, any ON exists as a polymer which has both hydrophobic and hydrophilic activities. Phosphorothioation (depicted in the chemical structure in this figure) serves to increase the hydrophobicity of the ON polymer but does not affect the hydrophilicity.
FIG. 14B conceptualizes the nature of oligonucleotide chelation of divalent and trivalent metal cations. Metal cations (represented by grey solid circles) link the hydrophilic surfaces of ON polymers via metal ion bridges (represented by ellipses) between two or three non-bridging oxygen or sulfur atoms in the phosphodiester linkages.

Herein is presented the discovery that oligonucleotides in aqueous solutions containing any simple metal cation that is divalent (such as for example but not limited to, $Ca^{2+}$, $Mg^{2+}$, $Fe^{2+}$) do not exist as salts but rather as chelated complexes of ONs. These complexes are comprised of oligonucleotide dimers or higher order molecular organizations in which ONs are linked at their phosphodiester backbones via divalent metal ion bridges (see FIG. 14B). At specific ON and metal cation concentrations, these chelated complexes are stable and soluble in aqueous solution and effectively sequester any divalent cations in the ON chelate complexes from solution interaction. This chelate complex formation is also likely to occur with simple metal cations with a 3+ charge or greater (as depicted in FIG. 14B). Thus ONs function as divalent cation chelaters and do not form salts with divalent cations.

Importantly, the formation of oligonucleotide chelate complexes does not occur with monovalent cations such as $Na^+$, $K^+$ or $NH_4^+$ and is thus unlikely to occur with any monovalent cation. Thus, the term "oligonucleotide salt" is specifically limited only to oligonucleotide salts with monovalent cations or with cations which do not form chelate complexes with oligonucleotides and is incorrectly used to describe oligonucleotides existing in solution or in powder form with divalent metal cations (or even trivalent metal cations).

The standard in the art clearly teaches the administration of ONs only as sodium salts. This is exemplified by the administration of numerous oligonucleotides in clinical trials as sodium salts which include Fomivirisen (ISIS 2922), Mipomersen (ISIS 301012), Trecovirsen (GEM 91), Custirsen (OGX-011/ISIS 112989), Genasense (G3139) and Aprinocarsem (ISIS 3531/LY 900003) (Geary et al., 2002, Clin. Pharmacokinetics, 41: 255-260; Yu et al., 2009, Clin. Pharmacokinetics, 48: 39-50; Sereni et al., 1999, J. Clin. Pharmacol., 39: 47-54; Chi et al., 2005, J. Nat. Canc. Inst., 97: 1287-1296; Marshall et al., 2004, Ann. Oncol., 15: 1274-1283; Grossman et al., 2004, Neuro-Oncol, 6: 32-40).

It is also provided herein a demonstration that the anti-coagulation of blood by oligonucleotides is caused by chelation of calcium by oligonucleotides as shown by the reversal of oligonucleotide-induced anti-coagulation by restoration of normal free calcium in blood by the addition of calcium chloride.

It is also provided herein a demonstration that the injection site reactions observed with subcutaneous injections of oligonucleotides (induration, inflammation, tenderness and pain) is due at least in part to local chelation of calcium and possibly other divalent cations such as magnesium at the injection site by oligonucleotides as shown by the inhibition of the injection site reactions (ISRs) by the injection of the ON prepared as a calcium chelate complex.

Fluorescence polarization is a common methodology used to examine intermolecular interactions. In this technique, the bait (i.e. any ON) is labeled with a fluorescent tag (e.g. FITC). In solution, the bait molecule tumbles freely in solution due to Brownian motion which results is poorly polarized fluorescence emission when the bait is subjected to excitation with the correct wavelength of light. With a ligand of sufficient molecular weight (at least the same size as the bait), the interaction between the bait and the ligand introduces a substantial inhibition of the tumbling of the complex in solution. As a result of this inhibited tumbling in solution, fluorescence emission becomes significantly polarized upon excitation. Thus with this technique, interactions can be measured in solution with no physical constraints on either binding partner. Fluorescence polarization is reported as the dimensionless mP, which is directly proportional to the fraction of bound bait molecules in the reaction. For example, if a very small fraction of bait molecules were bound by a particular ligand, there would be very little fluorescence polarization and consequently small mP values. At the other end of the spectrum, if a large proportion of bait molecules were bound by a particular ligand (or with a higher concentration of ligand), there would be substantial fluorescence polarization and consequently large mP values. In this fashion, binding isotherms for particular bait-ligand interactions can be generated by varying concentrations of ligand in the presence of a fixed amount of fluorescently tagged bait.

Herein diverse fluorescently labeled ONs are employed to examine their complex formation in the presence of monovalent and divalent cations. Although the monitoring of complex formation by fluorescence polarization requires these ONs to be fluorescently labeled, this label is affixed to the ON at the 3' end so as not to interfere with either the nitrogenous base or the phosphodiester backbone of the ON is question. Moreover the fluorescent tag is held away from the ON by a rigid 3 carbon linker to further exclude any perturbation of normal ON behavior in solution. Thus any ON complex formation observed herein using fluorescence polarization with a fluorescently labeled ON is an accurate representation of the solution behavior of unlabeled ONs (whether complexed or not).

The term oligonucleotide (ON) refers to an oligomer or polymer of ribonucleic acid (RNA) and/or deoxyribonucleic acid (DNA) and/or analogs thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

In the present application, the term "degenerate oligonucleotide" is intended to mean a single stranded oligonucleotide having a wobble (N) at every position, such as NNNNNNNNNN. Each base is synthesized as a wobble such that this ON actually exists as a population of different randomly generated sequences of the same length and physiochemical properties. For example, for an ON degenerate 40 bases in length, any particular sequence in the population would theoretically represent only $1/4^{40}$ or $8.3 \times 10^{-25}$ of the total fraction. Given that 1 mole=$6.022 \times 10^{23}$ molecules, and the fact that no synthesis of degenerates has exceeded 2 mmoles to date, any oligonucleotide with a specific sequence present effectively does not exist more than once in any preparation. Thus any complex formation observed in such a preparation must be due to the non-sequence dependent (or independent of the sequence) physiochemical properties of oligonucleotides since any particular oligonucleotide of a defined sequence, being unique in the preparation, cannot be expected to contribute any activity derived from its specific nucleotide sequence.

As further illustration of this concept, Example I compares the characterization of REP 2006 (a 40mer ON with a degenerate phosphorothioated sequence) with a 21mer of a defined sequence by high pressure liquid chromatography and mass spectrometry and clearly shows that any ON with a similar size and chemical modification (i.e. phosphorothioation) will have highly similar (if not identical) physiochemical features which are not affected by the sequence of nucleotides present.

Oligonucleotides can include various modifications, e.g., stabilizing modifications, and thus can include at least one modification in the phosphodiester linkage and/or on the sugar, and/or on the base. For example, the oligonucleotide can include, without restriction, one or more phosphorothioate linkages, phosphorodithioate linkages, and/or methylphosphonate linkages. Different chemically compatible modified linkages can be combined, e.g., modifications where the synthesis conditions are chemically compatible. While modified linkages are useful, the oligonucleotides can include phosphodiester linkages where the general physiochemical properties of the oligonucleotide polymer are not substantially affected. Additional useful modifications include, without restriction, modifications at the 2'-position of the sugar, such as 2'-O-alkyl modifications such as 2'-O-methyl modifications, 2'-amino modifications, 2'-halo modifications such as 2'-fluoro; acyclic nucleotide analogs. Other modifications are also known in the art and can be used such as locked nucleic acids. In particular, the oligonucleotide has modified linkages throughout, e.g., phosphorothioate; has a 3'- and/or 5'-cap; includes a terminal 3'-5' linkage; the oligonucleotide is or includes a concatemer consisting of two or more oligonucleotide sequences joined by a linker(s).

It is also provided a pharmaceutical ON composition which prevents oligonucleotide-induced anti-coagulation using a therapeutically effective amount of a pharmacologically acceptable oligonucleotide chelate complex as described herein prepared using any of the following metal cations: calcium, magnesium, cobalt, manganese, iron, copper, and/or zinc. The ON chelate complex may also be prepared using two or more different cations as described above. In particular, the pharmaceutical compositions are approved for administration to a human, or a non-human animal such as a non-human primate.

It is also provided a pharmaceutical ON composition which prevents the injection site reaction with subcutaneous administration containing a therapeutically effective amount of a pharmacologically acceptable ON chelate complex as described herein prepared using any of any of the following metal cations: calcium, magnesium, cobalt, manganese, iron, copper, and/or zinc. The ON chelate complex may also be prepared using two or more different cations as described above. In particular, the pharmaceutical compositions are approved for administration to a human, or a non-human animal such as a non-human primate.

It is also provided a pharmaceutical ON composition which improved IV infusion tolerability containing a therapeutically effective amount of a pharmacologically acceptable ON chelate complex prepared using any of the following metal cations: calcium, magnesium, cobalt, manganese, iron, copper, and/or zinc. The ON chelate complex may also be prepared using two or more different cations as described above. In particular, the pharmaceutical compositions are approved for administration to a human, or a non-human animal such as a non-human primate.

It is also provided a pharmaceutical ON composition which prevents oligonucleotide-induced deficiency of calcium, magnesium, iron, manganese, copper or zinc using a therapeutically effective amount of a pharmacologically acceptable ON chelate complex using any of the following metal cations: calcium, magnesium, cobalt, manganese, iron, copper, and/or zinc. The ON chelate complex may also be prepared using two or more different cations as described above. In particular, the pharmaceutical compositions are approved for administration to a human, or a non-human animal such as a non-human primate.

It is also provided a pharmaceutical ON composition with improved storage stability containing a therapeutically effective amount of a pharmacologically acceptable ON chelate complex using any of the following metal cations: calcium, magnesium, cobalt, manganese, iron, copper, and/or zinc. The ON chelate complex may also be prepared using two or more different cations as described above. In particular, the pharmaceutical compositions are approved for administration to a human, or a non-human animal such as a non-human primate.

It is also provided a pharmaceutical ON composition with lowered serum ½ life or reduced interaction with serum proteins containing a therapeutically effective amount of a pharmacologically acceptable ON chelate complex using any of the following metal cations: calcium, magnesium, cobalt, manganese, iron, copper, and/or zinc. The ON chelate complex may also be prepared using two or more different cations as described above. In particular, the pharmaceutical compositions are approved for administration to a human, or a non-human animal such as a non-human primate.

Furthermore, the above compositions may include physiologically and/or pharmaceutically acceptable carriers, adjuvant, vehicle and/or excipient. The characteristics of the carrier may depend on the route of administration. The term "pharmaceutically acceptable carrier, adjuvant, vehicle and/or excipient" refers to a carrier, adjuvant, vehicle or excipient that may be administered to a subject, incorporated into a composition of the present invention, and which does not destroy the pharmacological activity thereof. Pharmaceutically acceptable carriers, adjuvants, vehicles and excipients that may be used in the pharmaceutical compositions described herein include, but are not limited to, the following: ion exchangers, alumina, aluminum stearate, lecithin, self-emulsifying drug delivery systems ("SEDDS"), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the compositions of the present invention.

The compositions described herein may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compositions described herein may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compositions may, for example, be administered in a form suitable for immediate release or extended release. Immediate release or extended release may be achieved by the use of suitable pharmaceutical compositions, or, particularly in the case of extended release, by the use of devices such as subcutaneous implants or osmotic pumps. Thus, the above compositions may be adapted for administration by any one of the following routes: intraocular, oral ingestion, enteric, inhalation, cutaneous injection, subcutaneous injection, intramuscular injection, intraperitoneal injection, intrathecal injection or infusion, intratracheal, intravenous injection or infusion, or topically Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compositions may also be delivered through the oral cavity by sublingual and/or buccal administration. Molded tablets, compressed tablets or freeze-dried tablets are exemplary forms which may be used. Exemplary compositions include those formulating the present compositions with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

The effective amount of a compound described herein may be determined by one of ordinary skill in the art, and includes exemplary dosage amounts for an adult human of from about 0.1 to 500 mg/kg of body weight of active compound per day, which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion and clearance, drug combination, and severity of the particular condition. Preferred subjects for treatment include animals, most preferably mammalian species such as humans, and domestic animals such as dogs, cats and the like, subject to angiogenic dependent or angiogenic associated disorders.

The pharmaceutical composition may also contain other active factors and/or agents which enhance activity. Pharmaceutical compositions and formulations for administration may include transdermal patches, ointments, lotions, creams, gels, drops, suppositories, sprays, liquids, powders and aerosols. Conventional pharmaceutical carriers, aqueous, powder or oily bases, thickeners and the like may be necessary or desirable. Other formulations include those in which the ONs are mixed with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP, dioleoylphosphatidyl ethanolamine DOTMA) and other delivering agents or molecules. ONs may be encapsulated within liposomes or may form complexes thereto, in particular to cationic liposomes. Alternatively, ONs may be complexed to lipids, in particular to cationic lipids. Preferred fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof.

The present disclosure will be more readily understood by referring to the following examples.

EXAMPLE I

Characterization of Degenerate ON

Figure 1A:
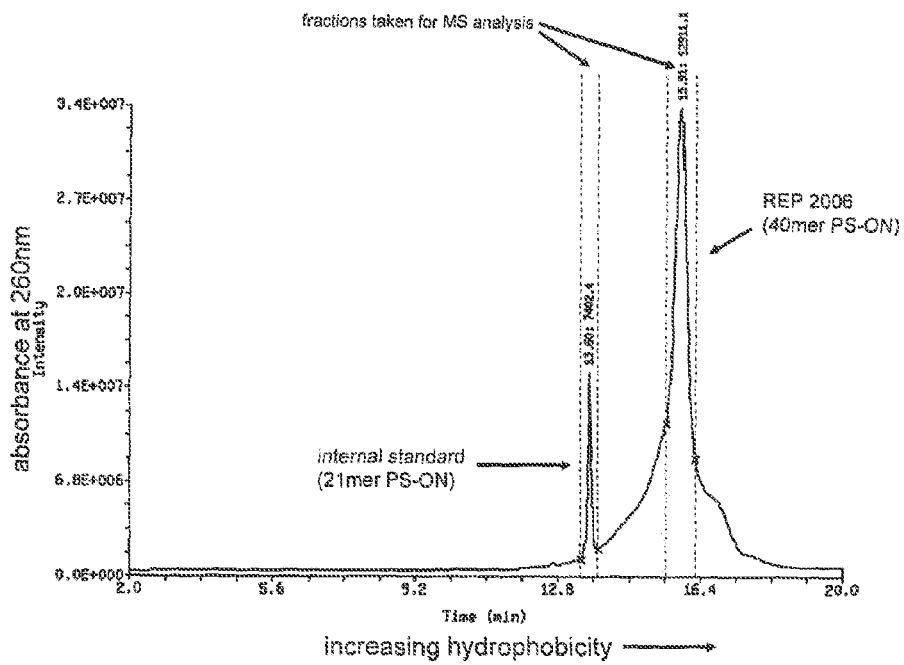
FIG. 1A) Co-separation of REP 2006 and a 21mer phosphorothioate ON with a defined sequence by high performance liquid chromatography.

FIG. 1A details the separation by HPLC (using a hydrophobic column) of two oligonucleotide preparations which are co-injected into the column at the same time. The first of these is called the internal standard and is a 21mer phosphorothioate oligonucleotide with a specific defined sequence, the second is REP 2006 (a 40mer degenerate phosphorothioate oligonucleotide). Both of these species separate into distinct defined peaks based only on their physiochemical properties (i.e. size and hydrophobicity); the sequence of nucleotides present in each of these ONs has NO meaningful impact on their physiochemical properties and therefore has NO impact on their separation. As such, the internal standard elutes off the column as a tightly defined peak with smaller retention time as compared to REP 2006, only due to the difference in the size of these two ON polymers. Note that the shoulders on either side of the REP 2006 peak are due to failure sequences typical in the production of longer oligonucleotides. Despite the heterogeneous sequence nature of REP 2006, it resolves as a similarly well defined peak by HPLC as the 21 mer specific sequence which illustrates the common physiochemical properties of all species in the REP 2006 preparation, even though there are a very large number of different sequences present. Subsequent to the HPLC separation of the REP 2006 and 21-mer peaks, these can be subjected to mass spectroscopy (MS) to identify the species present within these defined peaks (FIGS. 1B and 1C).

Figure 1B:
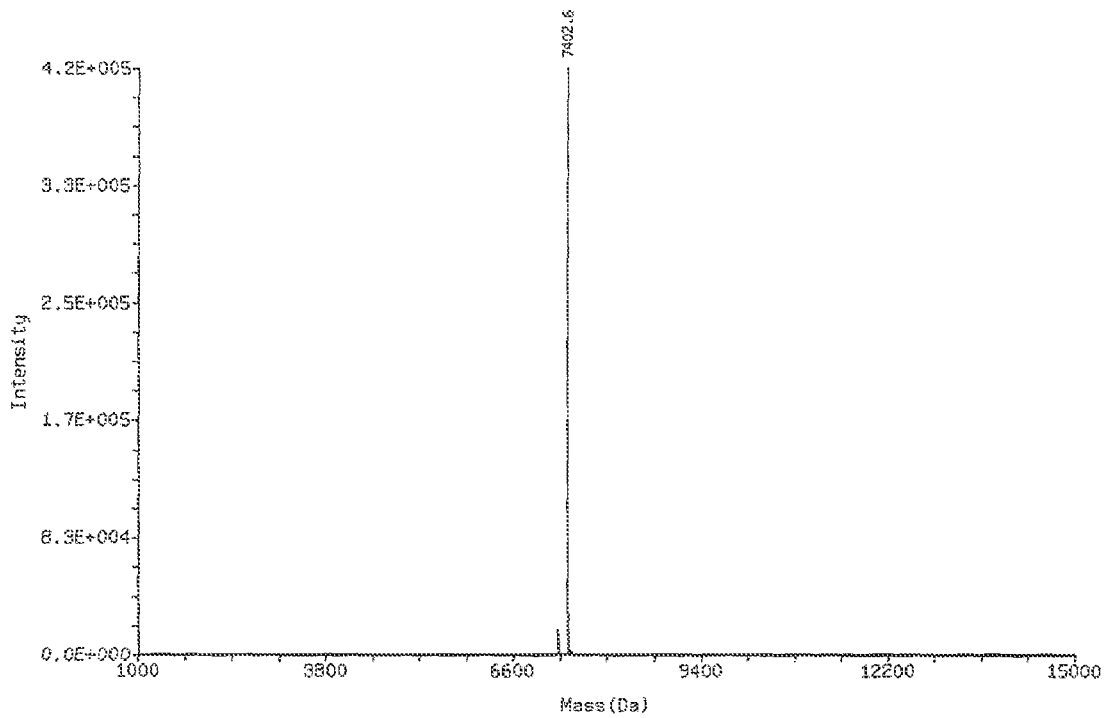
FIG. 1B) Identification of species in the 21mer ON by mass spectroscopy.
Figure 1C:
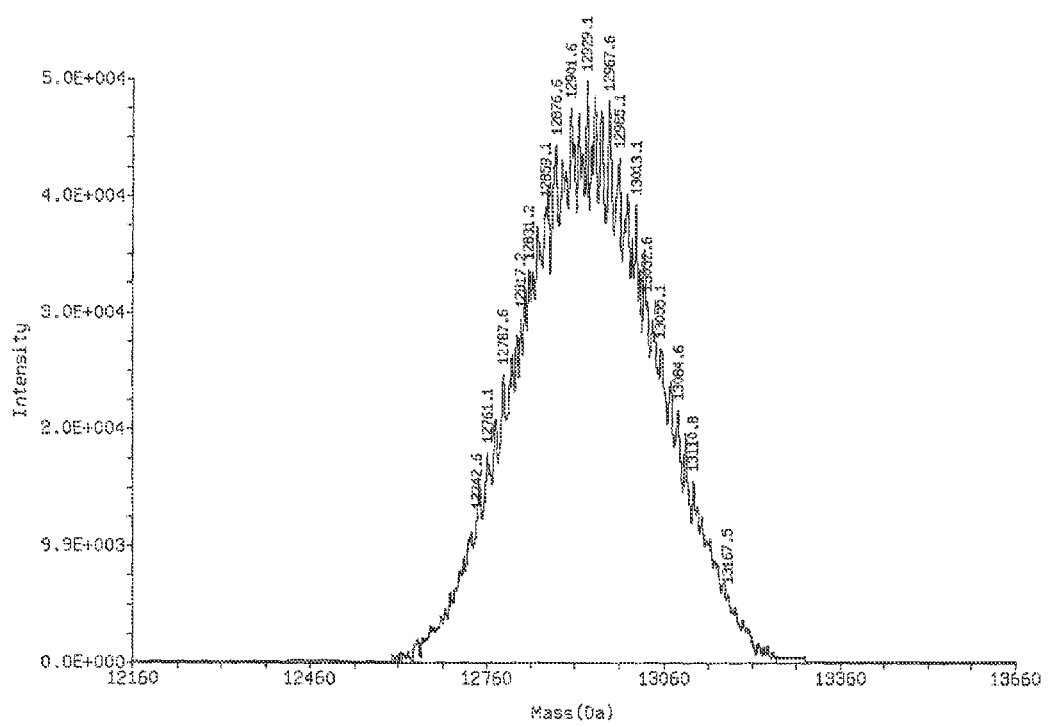
FIG. 1C) Identification of species in the REP 2006 ON by mass spectroscopy.
Figure 2A:
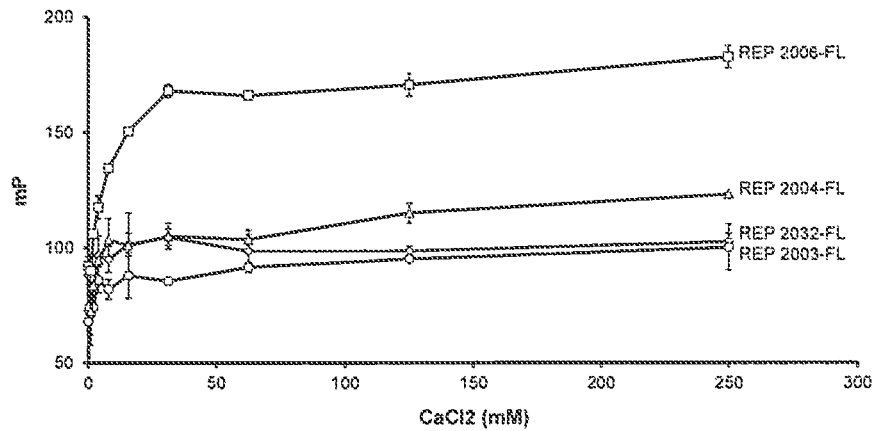
FIG. 2A) of various sizes timer (REP 2032-FL), 10mer (REP 2003-FL), 20mer (REP 2004-FL), 40mer (REP 2006-FL) and FIG. 2B) of fluorescently labeled degenerate ONs utilizing phosphorothioation (REP 2006-FL), phosphorothioation+2' O methyribose (REP 2107-FL) or 2' O methylribose (REP 2086-FL) and different sequences (poly C-REP 2031-FL; SEQ ID NO:4). The non-sequence dependent nature of the ON chelate complex formation was demonstrated by using degenerate oligonucleotides but is also demonstrated using a sequence specific oligonucleotide (REP 2031; SEQ ID NO:4). The formation of ON-calcium chelate complexes was demonstrated by combining increasing concentrations of ACS grade calcium chloride with FITC-labeled oligonucleotides in solution and monitoring oligonucleotide chelate complex formation by an increase in fluorescence polarization as described in Example 1. Values represent average+/− standard deviation from duplicate measurements.
Figure 2B:
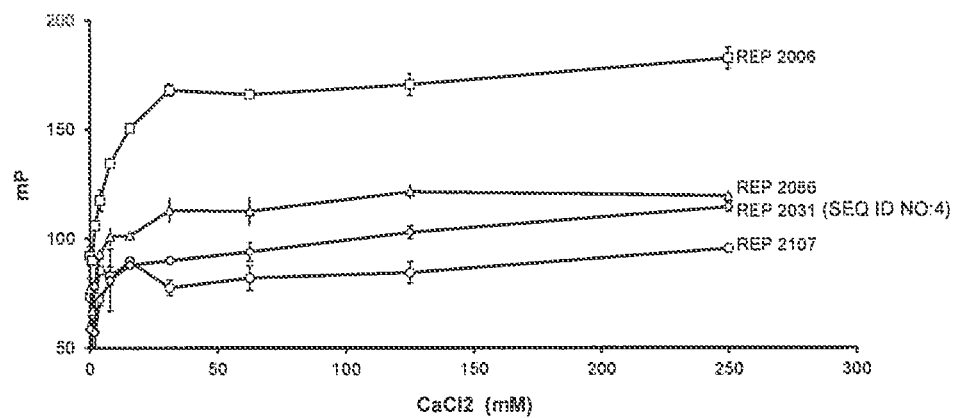
FIG. 2 illustrates the formation of ON-calcium chelate complexes by fluorescently labeled degenerate phosphorothioate ONs.
Figure 3A:
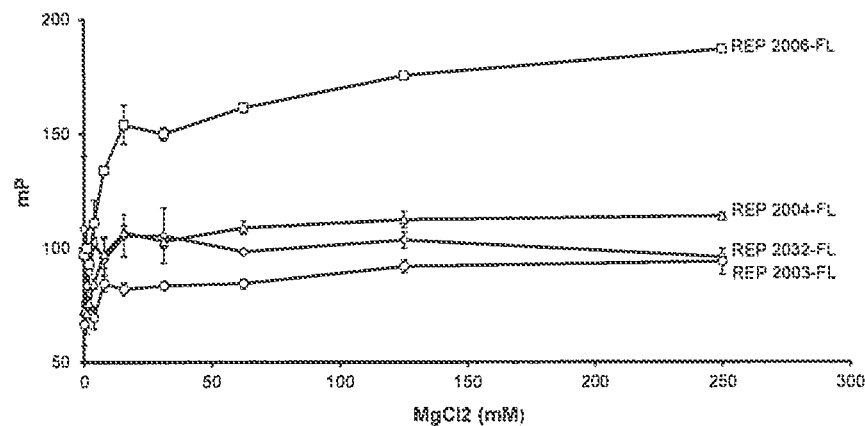
FIG. 3A) of various sizes 6mer (REP 2032-FL), 10mer (REP 2003-FL), 20mer (REP 2004-FL), 40mer (REP 2006-FL) and FIG. 3B) of fluorescently labeled degenerate ONs utilizing phosphorothioation (REP 2006-FL), phosphorothioation+2' O methyribose (REP 2107-FL) or 2' O methyribose (REP 2086-FL) and different sequences (poly C-REP 2031-FL; SEQ ID NO:4). The non-sequence dependent nature of the ON chelate complex formation was demonstrated by using degenerate oligonucleotides but is also demonstrated using a sequence specific oligonucleotide (REP 2031; SEQ ID NO:4). The formation of ON-magnesium chelate complexes was demonstrated by combining increasing concentrations of ACS grade magnesium chloride with FITC-labeled oligonucleotides in solution and monitoring oligonucleotide chelate complex formation by an increase in fluorescence polarization as described in Example 1. Values represent average+/− standard deviation from duplicate measurements.
Figure 3B:
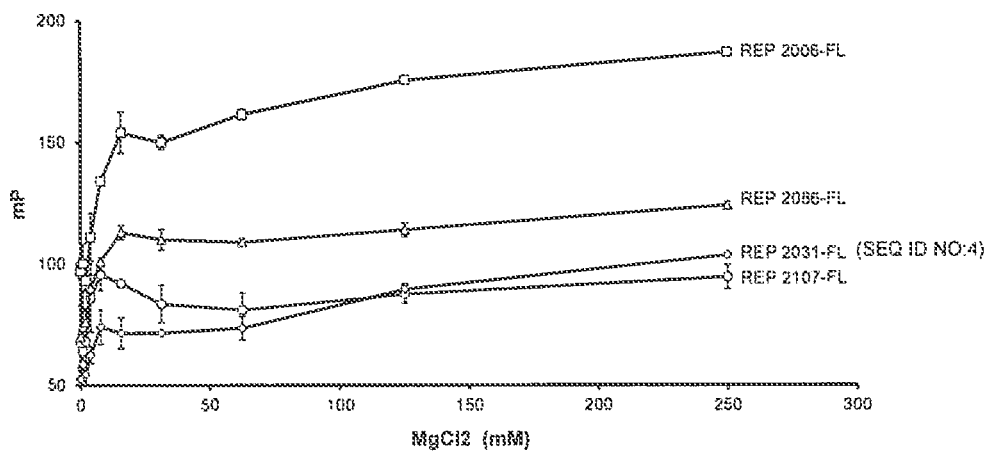
FIG. 3 illustrates the formation of ON-magnesium chelate complexes by fluorescently labeled degenerate phosphorothioate ONs.
Figure 4A:
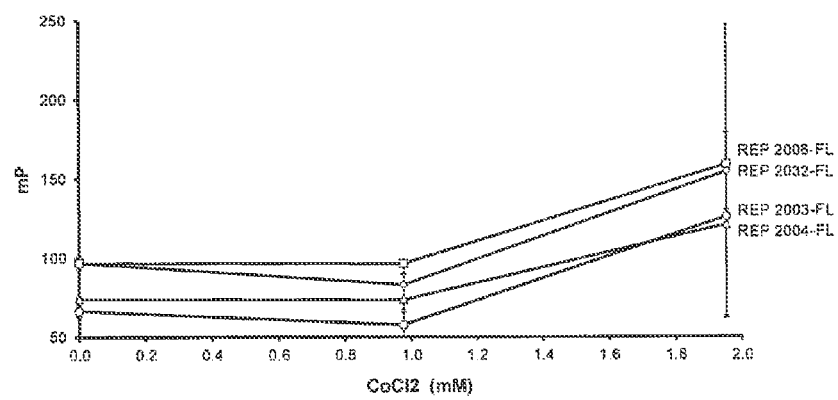
FIG. 4A) of various sizes 6mer (REP 2032-FL), 10mer (REP 2003-FL), 20mer (REP 2004-FL), 40mer (REP 2006-FL) and FIG. 4B) of fluorescently labeled degenerate ONs utilizing phosphorothioation (REP 2006-FL), phosphorothioation+2' O methyribose (REP 2107-FL) or 2' O methyribose (REP 2086-FL) and different sequences (poly C-REP 2031-FL; SEQ ID NO:4). The non-sequence dependent nature of the ON chelate complex formation was demonstrated by using degenerate oligonucleotides but is also demonstrated using a sequence specific oligonucleotide (REP 2031; SEQ ID NO:4). The formation of ON-cobalt chelate complexes was demonstrated by combining increasing concentrations of ACS grade cobalt chloride with FITC-labeled oligonucleotides in solution and monitoring oligonucleotide chelate complex formation by an increase in fluorescence polarization as described in Example 1. Values represent average+/− standard deviation from duplicate measurements.
Figure 4B:
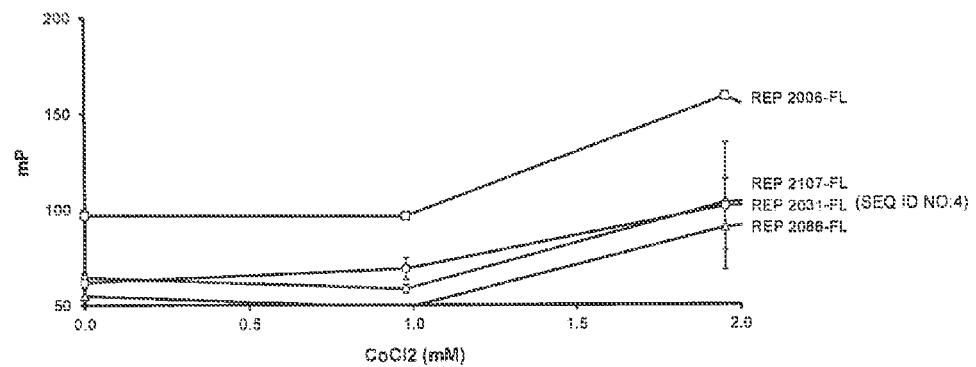
FIG. 4 illustrates the formation of ON-cobalt chelate complexes by fluorescently labeled degenerate phosphorothioate ONs.
Figure 5A:
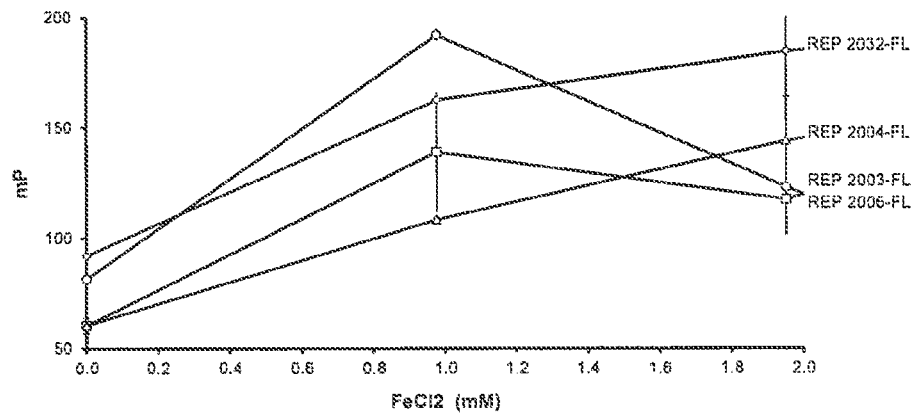
FIG. 5A) of various sizes 6mer (REP 2032-FL), 10mer (REP 2003-FL), 20mer (REP 2004-FL), 40mer (REP 2006-FL) and FIG. 5B) of fluorescently labeled degenerate ONs utilizing phosphorothioation (REP 2006-FL), phosphorothioation+2' O methyribose (REP 2107-FL) or 2' O methyribose (REP 2086-FL) and different sequences (poly C-REP 2031-FL; SEQ ID NO:4). The non-sequence dependent nature of the ON chelate complex formation was demonstrated by using degenerate oligonucleotides but is also demonstrated using a sequence specific oligonucleotide (REP 2031; SEQ ID NO 4). The formation of ON-iron chelate complexes was demonstrated by combining increasing concentrations of ACS grade iron chloride with FITC-labeled oligonucleotides in solution and monitoring oligonucleotide chelate complex formation by an increase in fluorescence polarization as described in Example 1. Values represent average+/− standard deviation from duplicate measurements.
Figure 5B:
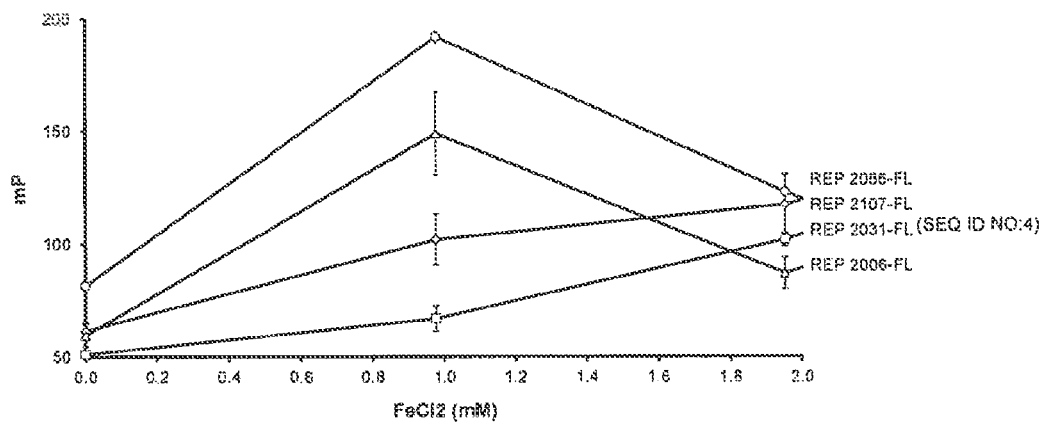
FIG. 5 illustrates the formation of ON-iron chelate complexes by fluorescently labeled degenerate phosphorothioate ONs.
Figure 6A:
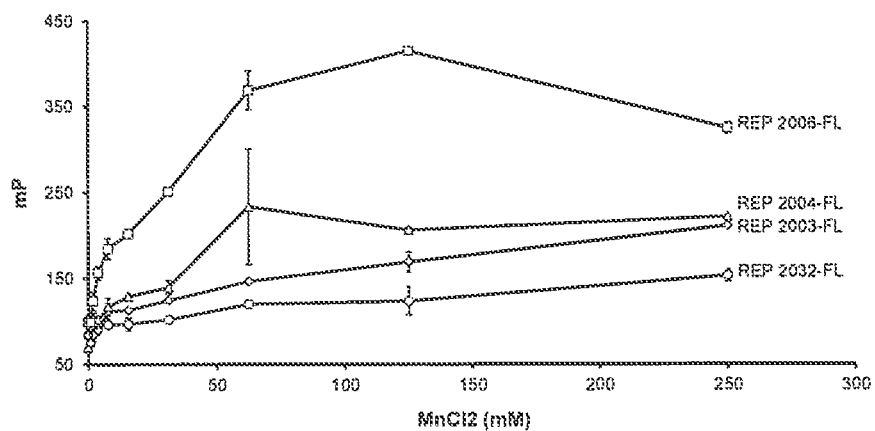
FIG. 6A) of various sizes 6mer (REP 2032-FL), 10mer (REP 2003-FL), 20mer (REP 2004-FL), 40mer (REP 2006-FL) and FIG. 6B) of fluorescently labeled degenerate ONs utilizing phosphorothioation (REP 2006-FL), phosphorothioation+2' O methyribose (REP 2107-FL) or 2' O methyribose (REP 2086-FL) and different sequences (poly C-REP 2031-FL; SEQ ID NO:4). The non-sequence dependent nature of the ON chelate complex formation was demonstrated by using degenerate oligonucleotides but is also demonstrated using a sequence specific oligonucleotide (REP 2031; SEQ ID NO:4). The formation of ON-manganese chelate complexes was demonstrated by combining increasing concentrations of ACS grade manganese chloride with FITC-labeled oligonucleotides in solution and monitoring oligonucleotide chelate complex formation by an increase in fluorescence polarization as described in Example 1. Values represent average+/− standard deviation from duplicate measurements.
Figure 6B:
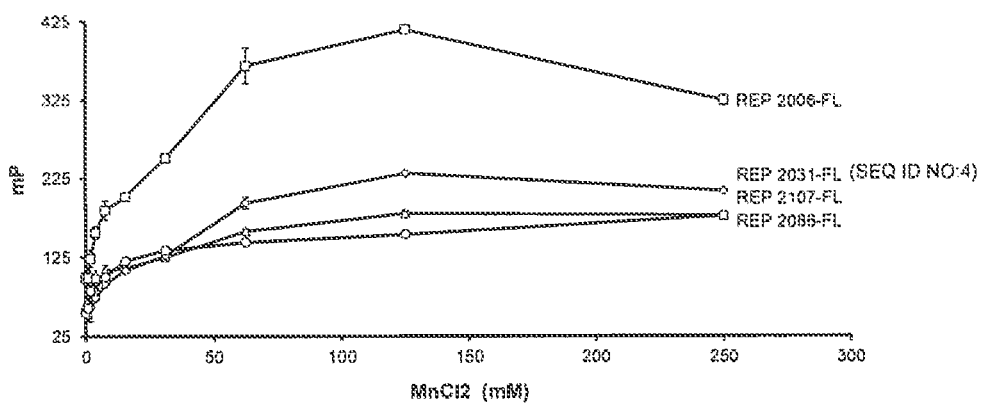
FIG. 6 illustrates the formation of ON-manganese chelate complexes by fluorescently labeled degenerate phosphorothioate ONs.
Figure 7A:
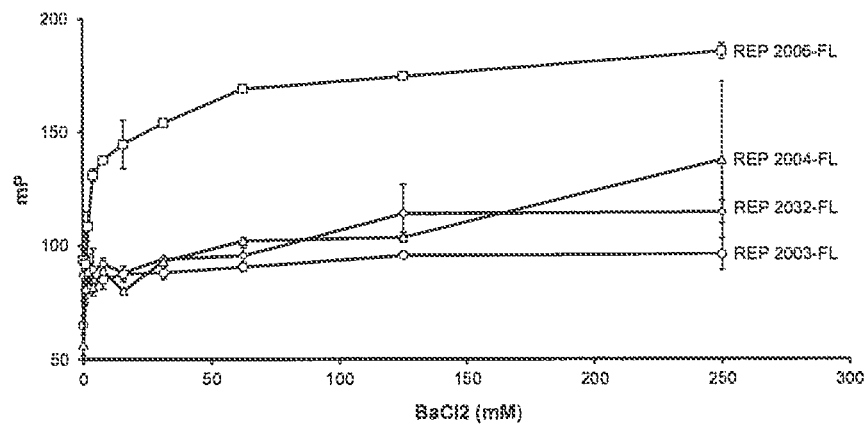
FIG. 7A) of various sizes 6mer (REP 2032-FL), 10mer (REP 2003-FL), 20mer (REP 2004-FL), 40mer (REP 2006-FL) and FIG. 7B) of fluorescently labeled degenerate ONs utilizing phosphorothioation (REP 2006-FL), phosphorothioation+2' O methyribose (REP 2107-FL) or 2' O methyribose (REP 2086-FL) and different sequences (poly C-REP 2031-FL; SEQ ID N:4). The non-sequence dependent nature of the ON chelate complex formation was demonstrated by using degenerate oligonucleotides but is also demonstrated using a sequence specific oligonucleotide (REP 2031; SEQ ID NO:4). The formation of ON-barium chelate complexes was demonstrated by combining increasing concentrations of ACS grade barium chloride with FITC-labeled oligonucleotides in solution and monitoring oligonucleotide chelate complex formation by an increase in fluorescence polarization as described in Example 1. Values represent average+/− standard deviation from duplicate measurements.
Figure 7B:
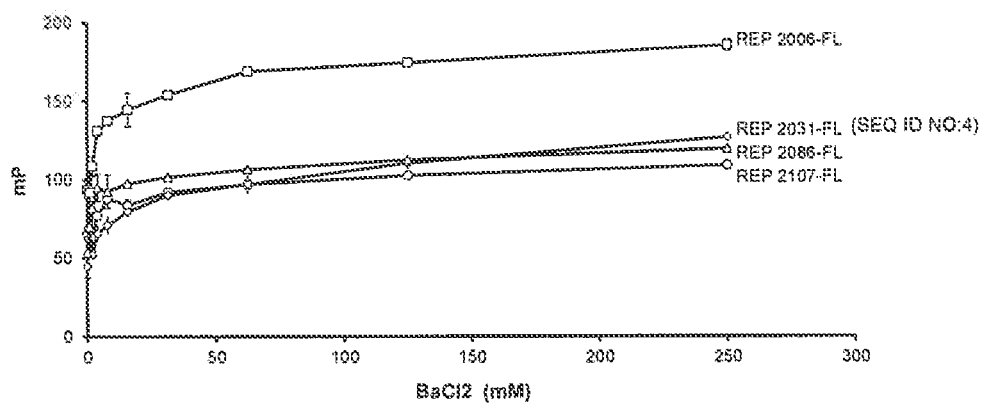
FIG. 7 illustrates the formation of ON-barium chelate complexes by fluorescently labeled degenerate phosphorothioate ONs.
Figure 8A:
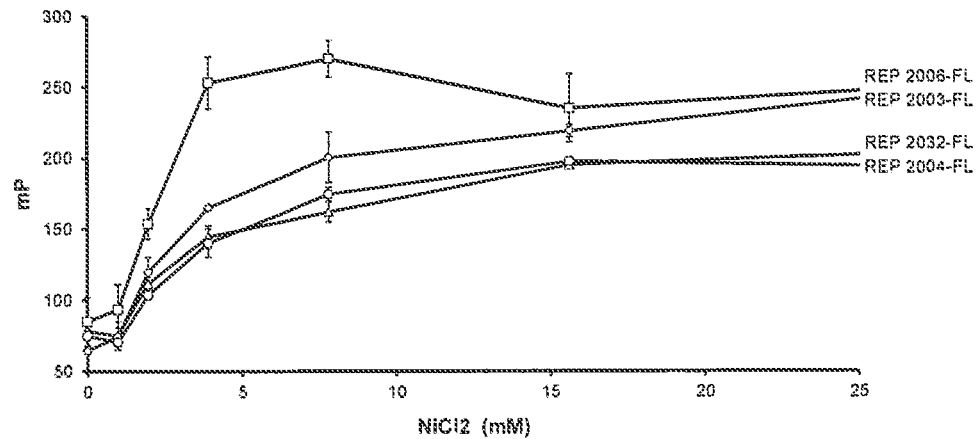
FIG. 8A) of various sizes 6mer (REP 2032-FL), 10mer (REP 2003-FL), 20mer (REP 2004-FL), 40mer (REP 2006-FL) and FIG. 8B) of fluorescently labeled degenerate ONs utilizing phosphorothioation (REP 2006-FL), phosphorothioation+2' O methyribose (REP 2107-FL) or 2' O methyribose (REP 2086-FL) and different sequences (poly C-REP 2031-FL; SEQ ID NO:4). The non-sequence dependent nature of the ON chelate complex formation was demonstrated by using degenerate oligonucleotides but is also demonstrated using a sequence specific oligonucleotide (REP 2031; SEQ ID NO:4). The formation of ON-nickel chelate complexes was demonstrated by combining increasing concentrations of ACS grade nickel chloride with FITC-labeled oligonucleotides in solution and monitoring oligonucleotide chelate complex formation by an increase in fluorescence polarization as described in Example 1. Values represent average+/− standard deviation from duplicate measurements.
Figure 8B:
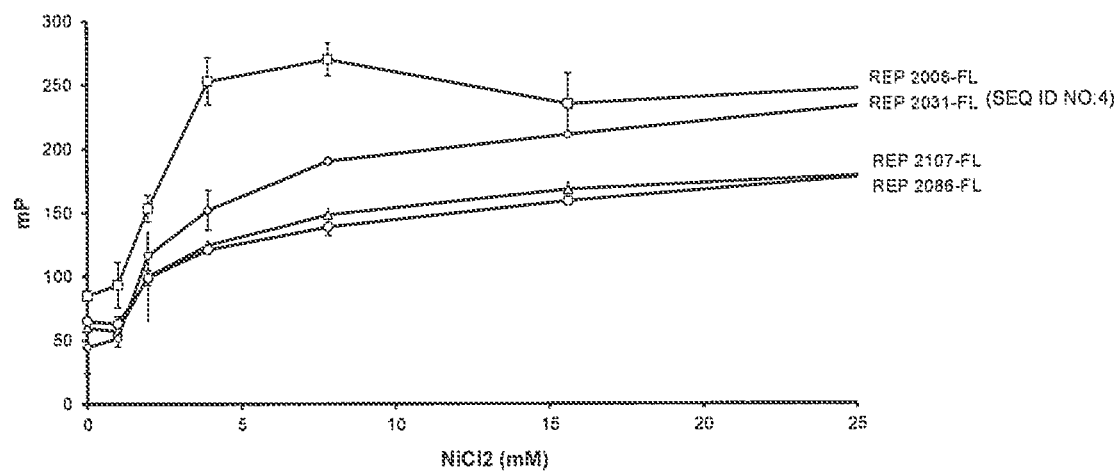
FIG. 8 illustrates the formation of ON-nickel chelate complexes by fluorescently labeled degenerate phosphorothioate ONs.
Figure 9A:
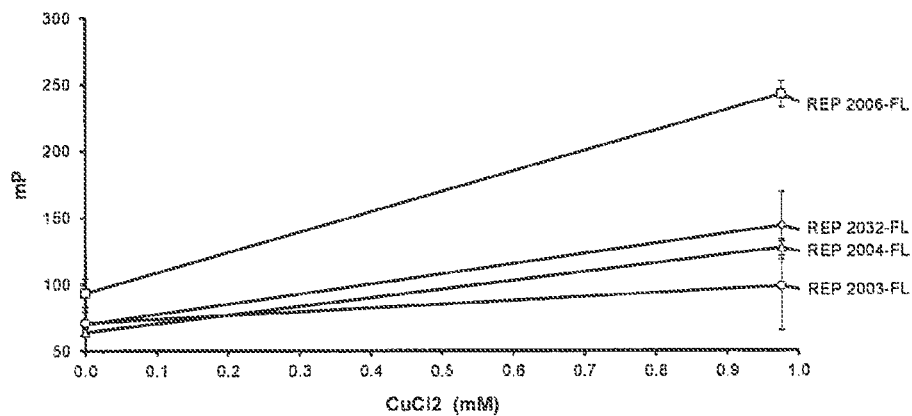
FIG. 9A) of various sizes 6mer (REP 2032-FL), 10mer (REP 2003-FL), 20mer (REP 2004-FL), 40mer (REP 2006-FL) and FIG. 9B) of fluorescently labeled degenerate ONs utilizing phosphorothioation (REP 2006-FL), phosphorothioation+2' O methyribose (REP 2107-FL) or 2' O methyribose (REP 2086-FL) and different sequences (poly C-REP 2031-FL; SEQ ID NO:4). The non-sequence dependent nature of the ON chelate complex formation was demonstrated by using degenerate oligonucleotides but is also demonstrated using a sequence specific oligonucleotide (REP 2031; SEQ ID NO:4). The formation of ON-copper chelate complexes was demonstrated by combining increasing concentrations of ACS grade copper chloride with FITC-labeled oligonucleotides in solution and monitoring oligonucleotide chelate complex formation by an increase in fluorescence polarization as described in Example 1. Values represent average+/− standard deviation from duplicate measurements.
Figure 9B:
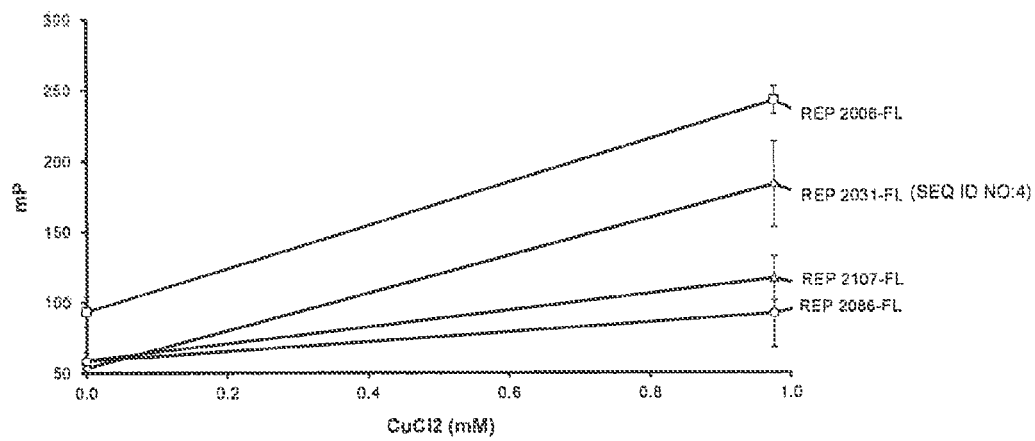
FIG. 9 illustrates the formation of ON-copper chelate complexes by fluorescently labeled degenerate phosphorothioate ONs.
Figure 10A:
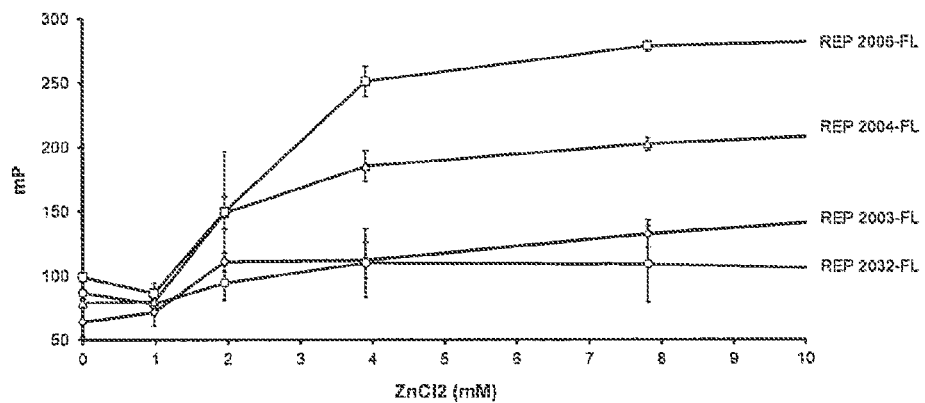
FIG. 10A) of various sizes 6mer (REP 2032-FL), 10mer (REP 2003-FL), 20mer (REP 2004-FL), 40mer (REP 2006-FL) and FIG. 10B) of fluorescently labeled degenerate ONs utilizing phosphorothioation (REP 2006-FL), phosphorothioation+2' O methyribose (REP 2107-FL) or 2' O methyribose (REP 2086-FL) and different sequences (poly C-REP 2031-FL; SEQ ID NO:4). The non-sequence dependent nature of the ON chelate complex formation was demonstrated by using degenerate oligonucleotides but is also demonstrated using a sequence specific oligonucleotide (REP 2031; SEQ ID NO:4). The formation of ON-zinc chelate complexes was demonstrated by combining increasing concentrations of ACS grade zinc chloride with FITC-labeled oligonucleotides in solution and monitoring oligonucleotide chelate complex formation by an increase in fluorescence polarization as described in Example 1. Values represent average+/− standard deviation from duplicate measurements.
Figure 10B:
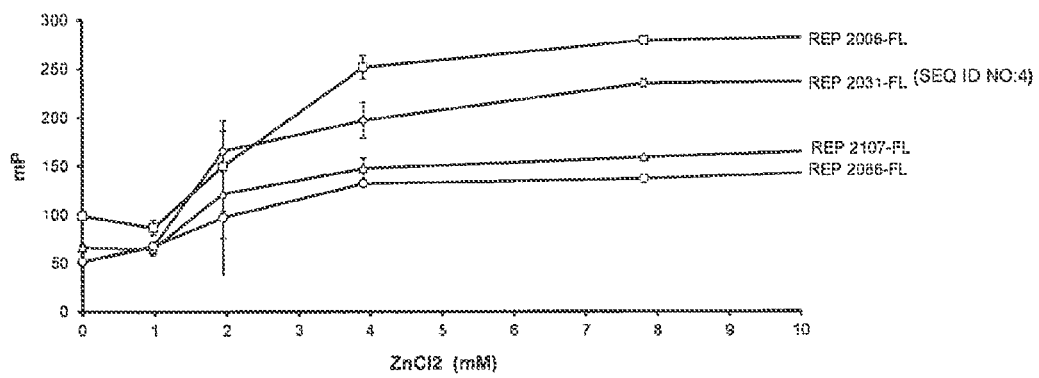
FIG. 10 illustrates the formation of ON-zinc chelate complexes by fluorescently labeled degenerate phosphorothioate ONs.
Figure 11A:
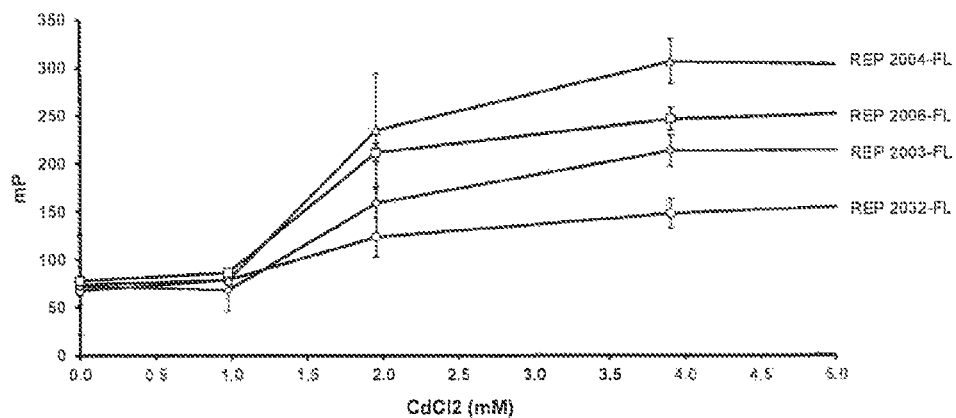
FIG. 11A) of various sizes 6mer (REP 2032-FL), 10mer (REP 2003-FL), 20mer (REP 2004-FL), 40mer (REP 2006-FL) and FIG. 11B) of fluorescently labeled degenerate ONs utilizing phosphorothioation (REP 2006-FL), phosphorothioation+2' O methyribose (REP 2107-FL) or 2' O methyribose (REP 2086-FL) and different sequences (poly C-REP 2031-FL; SEQ ID NO:4). The non-sequence dependent nature of the ON chelate complex formation was demonstrated by using degenerate oligonucleotides but is also demonstrated using a sequence specific oligonucleotide (REP 2031; SEQ ID NO:4). The formation of ON-cadmium chelate complexes was demonstrated by combining increasing concentrations of ACS grade cadmium chloride with FITC-labeled oligonucleotides in solution and monitoring oligonucleotide chelate complex formation by an increase in fluorescence polarization as described in Example 1. Values represent average+/− standard deviation from duplicate measurements.
Figure 11B:
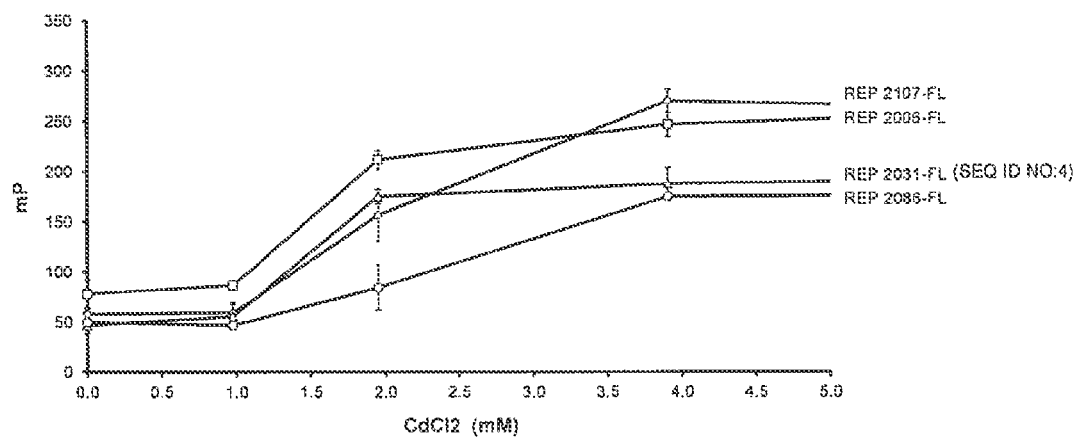
FIG. 11 illustrates the formation of ON-cadmium chelate complexes by fluorescently labeled degenerate phosphorothioate ONs.
Figure 12A:
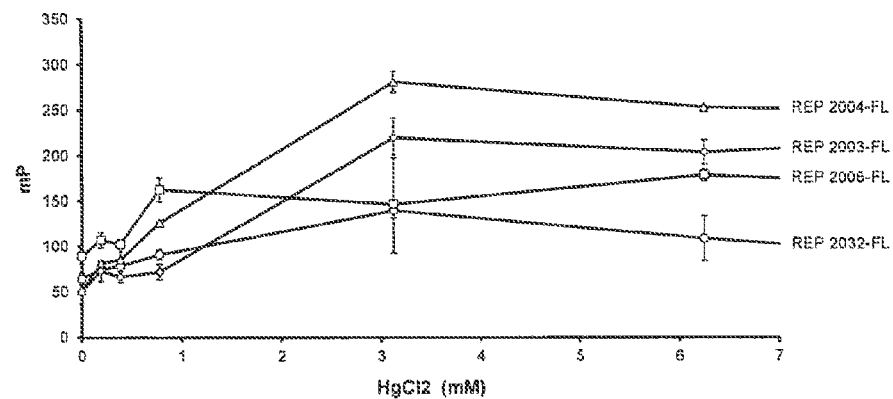
FIG. 12A) of various sizes 6mer (REP 2032-FL), 10mer (REP 2003-FL), 20mer (REP 2004-FL), 40mer (REP 2006-FL) and FIG. 12B) of fluorescently labeled degenerate ONs utilizing phosphorothioation (REP 2006-FL), phosphorothioation+2' O methyribose (REP 2107-FL) or 2' O methyribose (REP 2086-FL) and different sequences (poly C-REP 2031-FL; SEQ ID NO:4). The non-sequence dependent nature of the ON chelate complex formation was demonstrated by using degenerate oligonucleotides but is also demonstrated using a sequence specific oligonucleotide (REP 2031; SEQ ID NO:4). The formation of ON-mercury chelate complexes was demonstrated by combining increasing concentrations of ACS grade mercury chloride with FITC-labeled oligonucleotides in solution and monitoring oligonucleotide chelate complex formation by an increase in fluorescence polarization as described in Example 1. Values represent average+/− standard deviation from duplicate measurements.
Figure 12B:
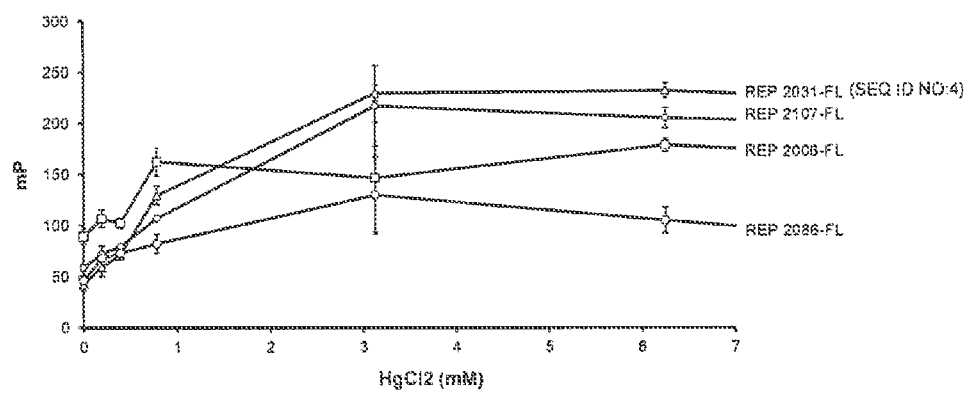
FIG. 12 illustrates the formation of ON-mercury chelate complexes by fluorescently labeled degenerate phosphorothioate ONs.
Figure 13A:
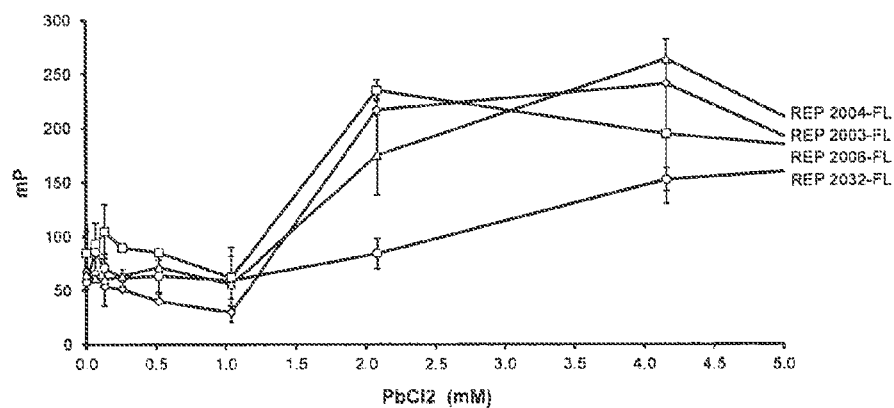
FIG. 13A) of various sizes timer (REP 2032-FL), 10mer (REP 2003-FL), 20mer (REP 2004-FL), 40mer (REP 2006-FL) and FIG. 13B) of fluorescently labeled degenerate ONs utilizing phosphorothioation (REP 2006-FL), phosphorothioation+2' O methyribose (REP 2107-FL) or 2' O methyribose (REP 2086-FL) and different sequences (poly C-REP 2031-FL; SEQ ID NO:4). The non-sequence dependent nature of the ON chelate complex formation was demonstrated by using degenerate oligonucleotides but is also demonstrated using a sequence specific oligonucleotide (REP 2031; SEQ ID NO:4). The formation of ON-lead chelate complexes was demonstrated by combining increasing concentrations of ACS grade lead chloride with FITC-labeled oligonucleotides in solution and monitoring oligonucleotide chelate complex formation by an increase in fluorescence polarization as described in Example 1. Values represent average+/− standard deviation from duplicate measurements.
Figure 13B:
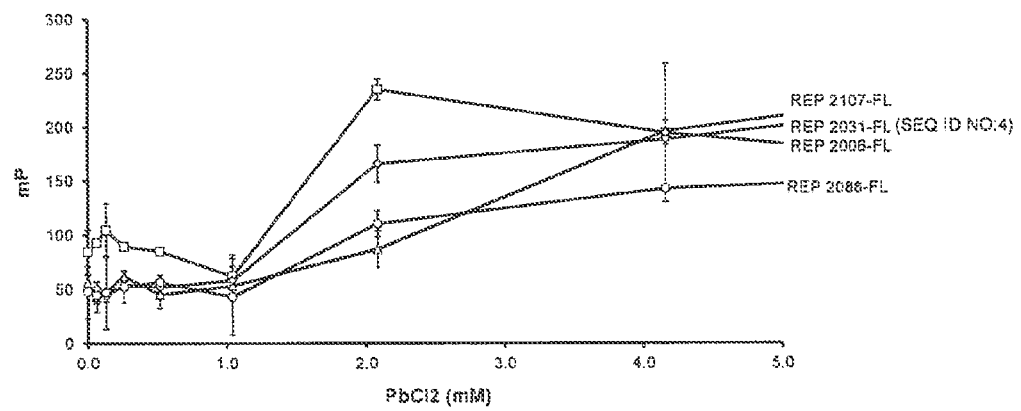
FIG. 13 illustrates the formation of ON-lead chelate complexes by fluorescently labeled degenerate phosphorothioate ONs.

In FIG. 1B, the 21mer is resolved into a single species with MW of 7402.6 Da, consistent with this PS-ON having a defined sequence. However, MS analysis of REP 2006 (FIG. 1C) reveals an extremely large number of species present whose mass range has an almost perfect normal distribution, consistent with its completely degenerate nature. This mass range goes from $C_{40}$ (the smallest species) to $A_{40}$ (the largest species) and the prevalence of these species are extremely small with the number of species increasing (peak intensity) as their mass approaches the center of the mass range. This is because an increasingly larger number of different sequences will result in a similar mass. The fact that all of the different ON species present in REP 2006 have the same retention time on a hydrophobic column during HPLC separation clearly demonstrates that all ONs of the same size and with the same chemical modifications (i.e. phosphorothioation) will have highly similar (if not identical) physiochemical properties and as such, can be considered functionally similar in any application or property which is not dependent on the sequence of nucleotides present in a particular ON molecule. Thus, any ON chelate complex formation observed with any particular degenerate ON (e.g. REP 2003, REP 2004), cannot be dependent on the sequence on oligonucleotides present and must be dependent on the conserved physiochemical properties of any ON.

EXAMPLE II

ONs Form Chelate Complexes with Diverse Divalent Metal Cations

The interaction of oligonucleotide ammonium salts with various divalent metal cations was examined by fluorescence polarization (FP) as described above. During oligonucleotide synthesis, each oligonucleotide was conjugated to fluorescein isothiocyanate (FITC) at the 3' end by a rigid 3 carbon linker using well established reagents and synthesis protocols. These oligonucleotides were cleaved from the synthesis and left as ammonium salts. The oligonucleotides used in this example are described in Table 1.

TABLE 1

ONs used in Example II

| Oligonucleotide | Sequence (5'-3') | Modifications |
|---|---|---|
| REP 2032-FL | $N_6$ | PS |
| REP 2003-FL | $N_{10}$ | PS |
| REP 2004-FL | $N_{20}$ | PS |
| REP 2006-FL | $N_{40}$ | PS |
| REP 2107-FL | $N_{40}$ | PS + 2' O Me |
| REP 2086-FL | $N_{40}$ | 2' O Me |
| REP 2031-FL | $C_{40}$ (SEQ ID NO: 4) | PS |

Figure 16:
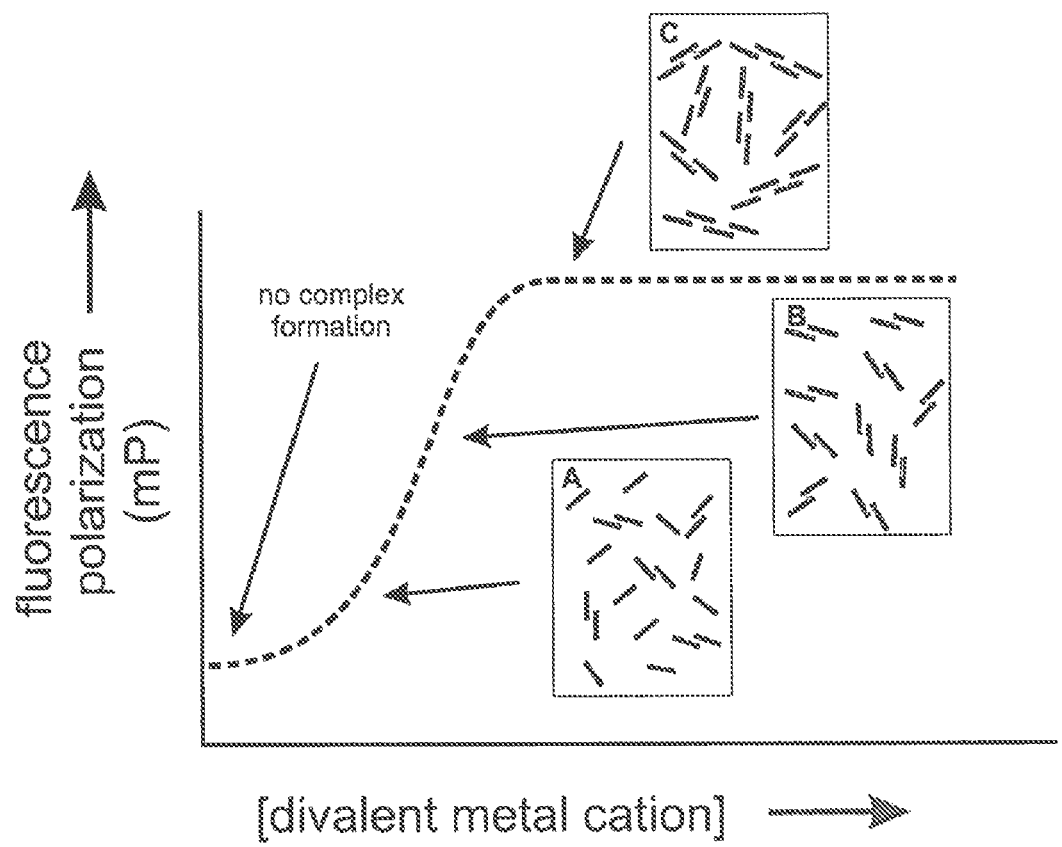
FIG. 16 illustrates the effect of the solution behavior of fluorescent-ON chelate complexes on fluorescence polarization. With increasing metal concentration, the size (and mass) of ON chelate complex formation also increases (see FIG. 15) and thus tumbles more slowly in solution. This slower tumbling of the complex in solution leads to increased fluorescence polarization and an increased mP value.
Figure 17A:
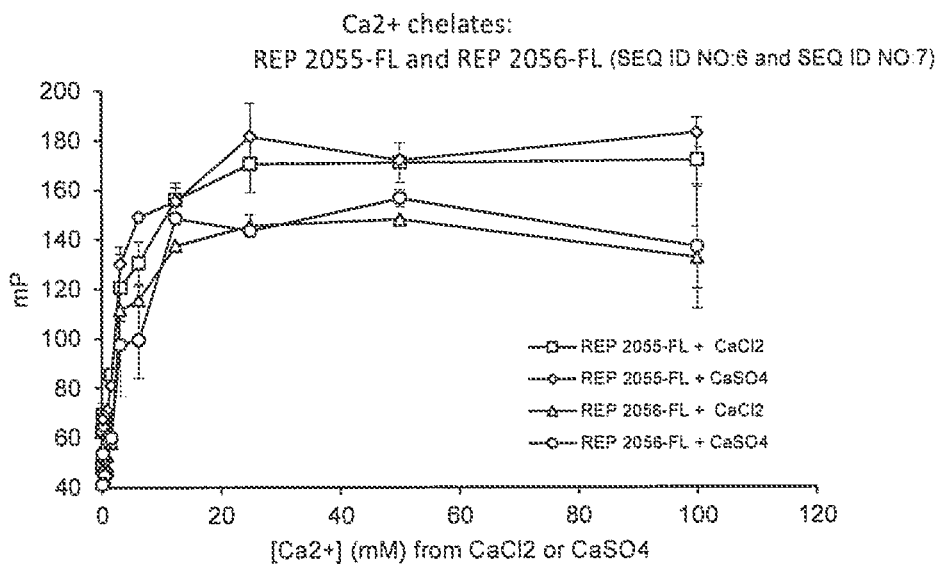
FIG. 17A) ON chelate complex formation with REP 2055-FL (SEQ ID NO:6) and REP 2056-FL (SEQ ID NO:7).
Figure 17B:
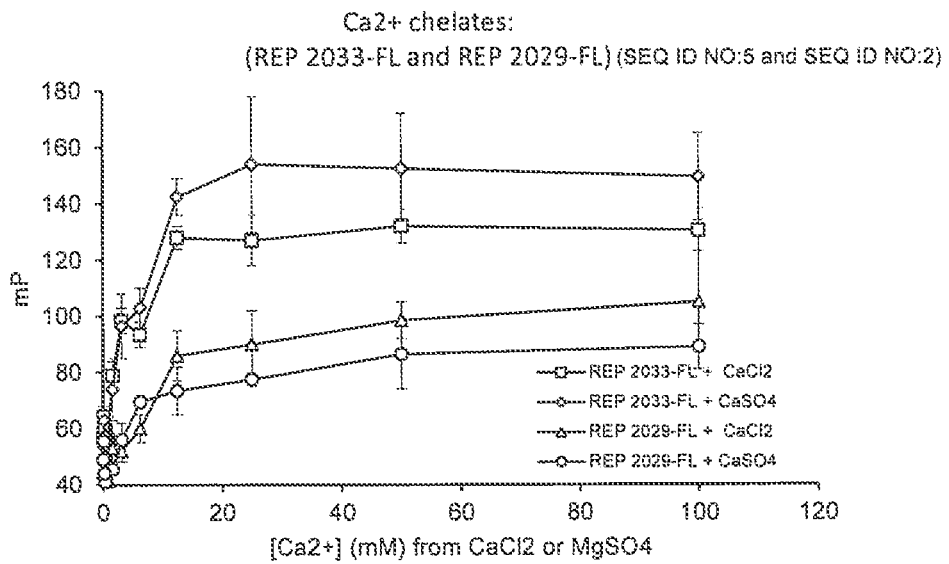
FIG. 17B) ON chelate complex formation with REP 2033-FL (SEQ ID NO:5) and REP 2029-FL (SEQ ID NO:2). Values represent average+/− standard deviation from duplicate measurements.
Figure 18A:
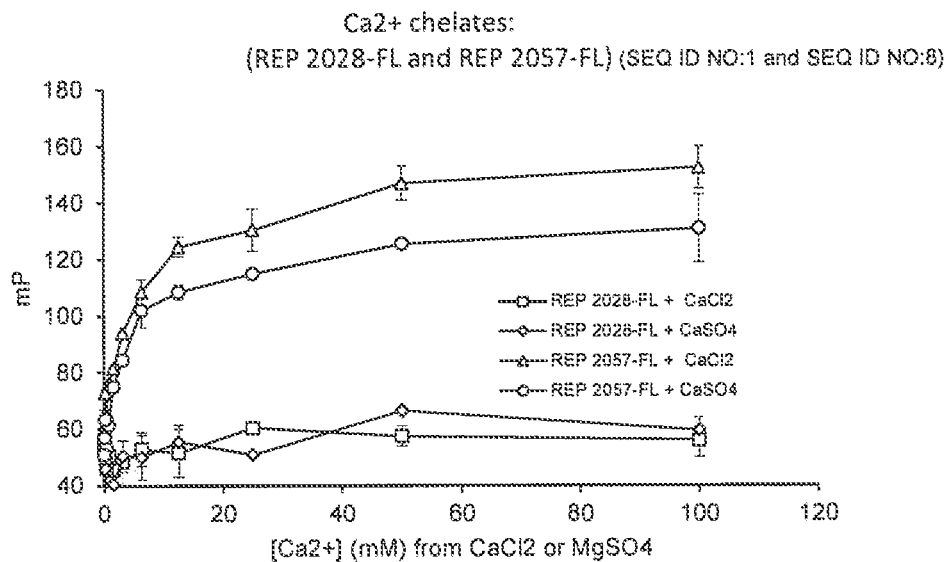
FIG. 18A) absence of ON chelate complex formation with REP 2028-FL and ON chelate complex formation with REP 2057-FL (SEQ ID NO:8).
Figure 18B:
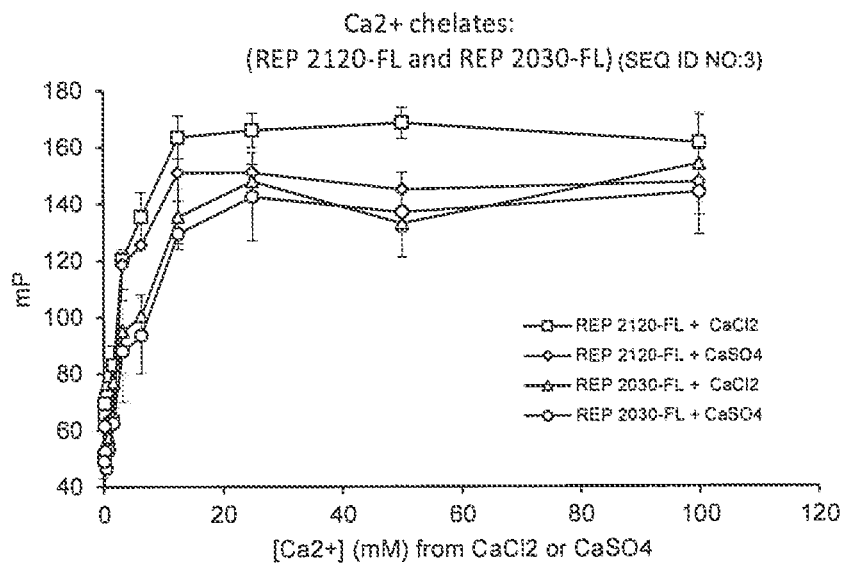
FIG. 18B) ON chelate complex formation with REP 2120-FL and REP 2030-FL. Values represent average+/− standard deviation from duplicate measurements.
Figure 19A:
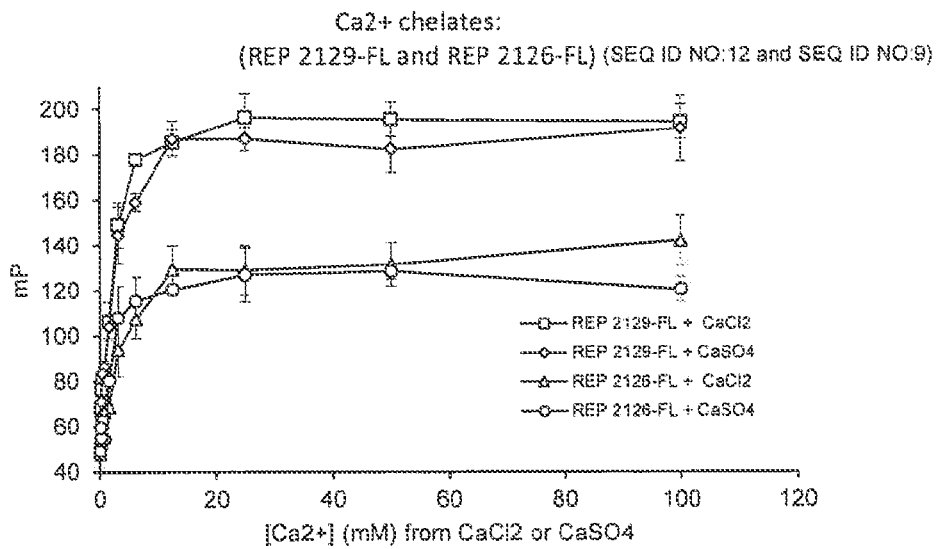
FIG. 19A) ON chelate complex formation with REP 2129-FL (SEQ ID NO:12) and REP 2126-FL (SEQ ID NO:9).
Figure 19B:
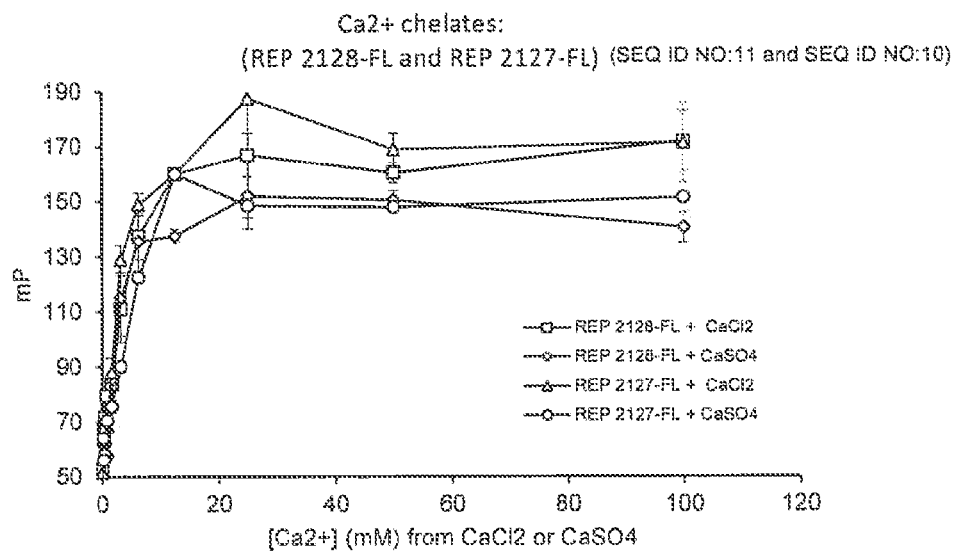
FIG. 19B) ON chelate complex formation with REP 2128-FL (SEQ ID NO:11) and REP 2127-FL (SEQ ID NO:10). Values represent average+/− standard deviation from duplicate measurements.
Figure 20A:
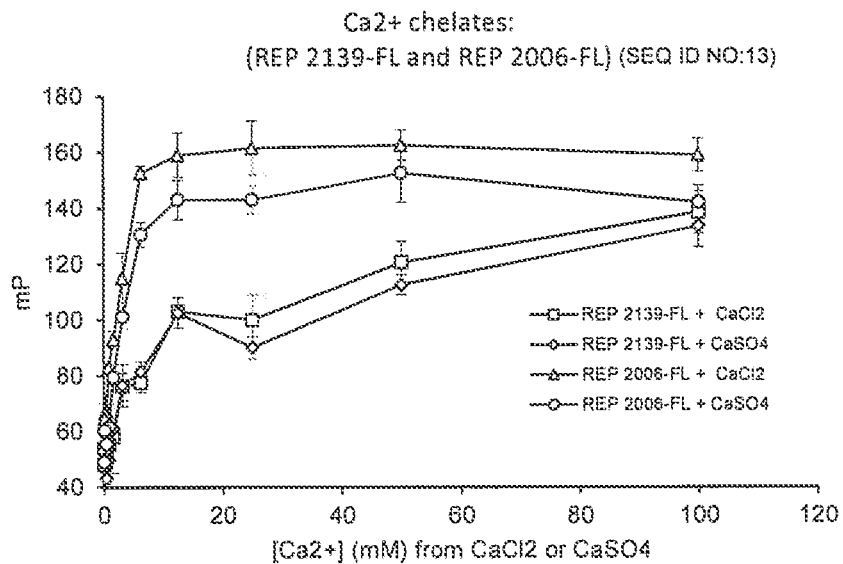
FIG. 20A) ON chelate with REP 2139-FL (SEQ ID NO:13) and REP 2006-FL.
Figure 20B:
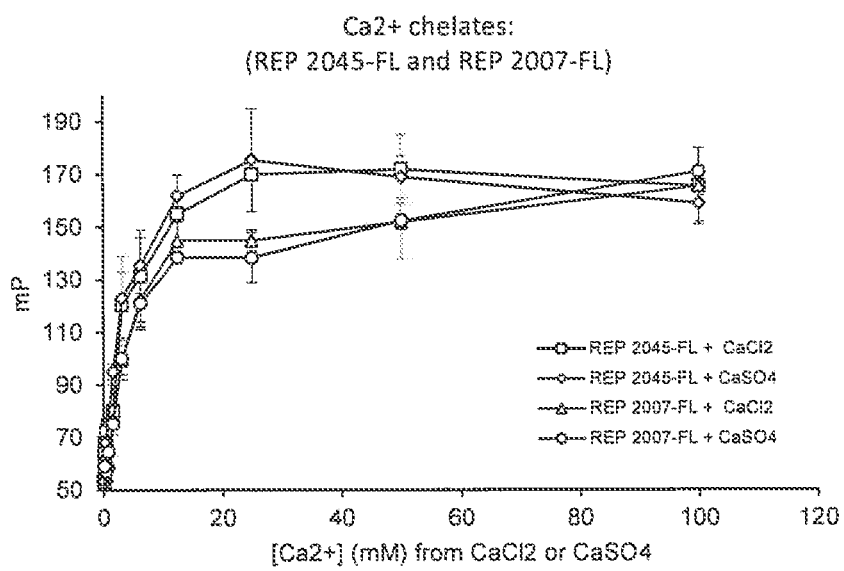
FIG. 20B) ON chelate complex formation with REP 2045-FL and REP 2007-FL. Values represent average+/− standard deviation from duplicate measurements.
Figure 21A:
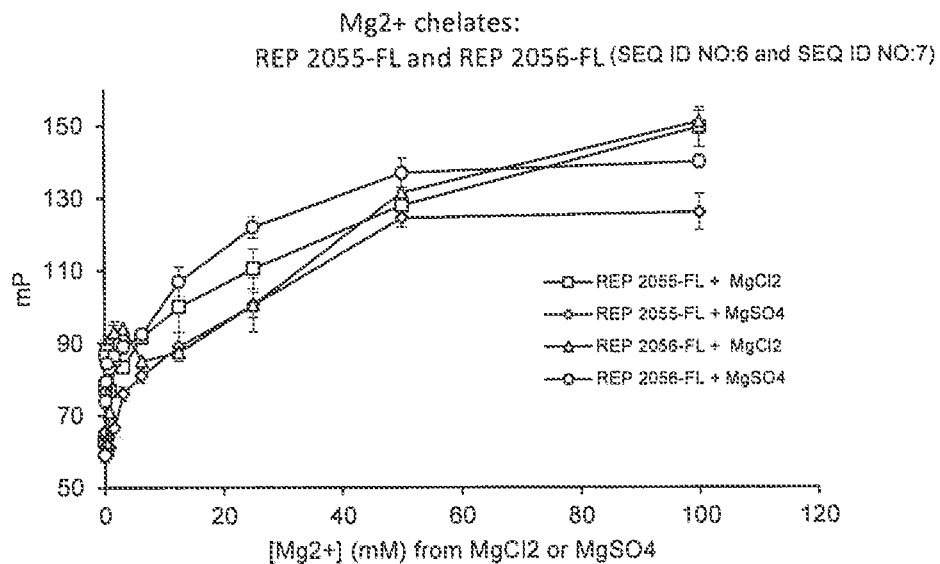
FIG. 21A) ON chelate complex formation with REP 2055-FL (SEQ ID NO:6) and REP 2056-FL (SEQ ID NO:7).
Figure 21B:
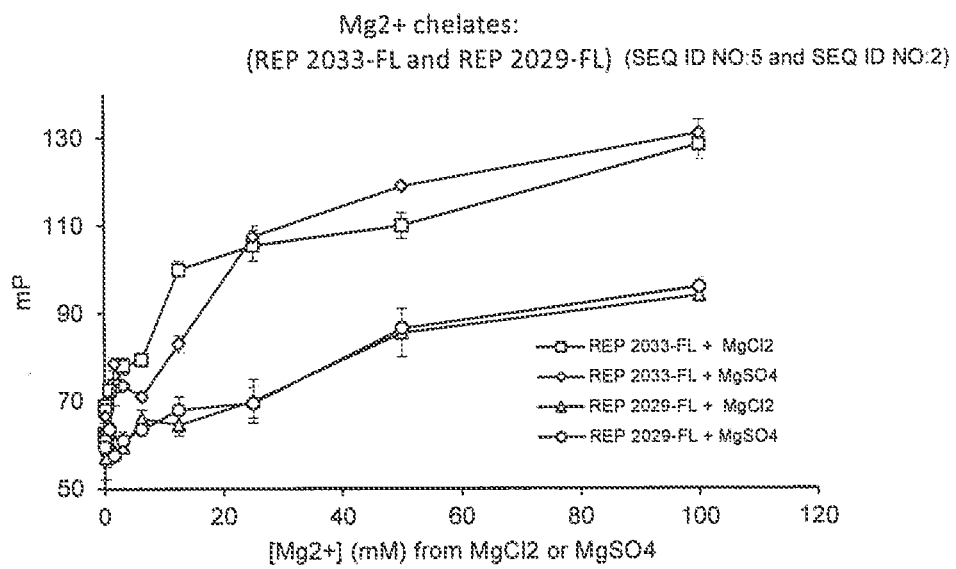
FIG. 21B) ON chelate complex formation with REP 2033-FL (SEQ ID NO:5) and REP 2029-FL (SEQ ID NO:12). Values represent average+/− standard deviation from duplicate measurements.
Figure 22A:
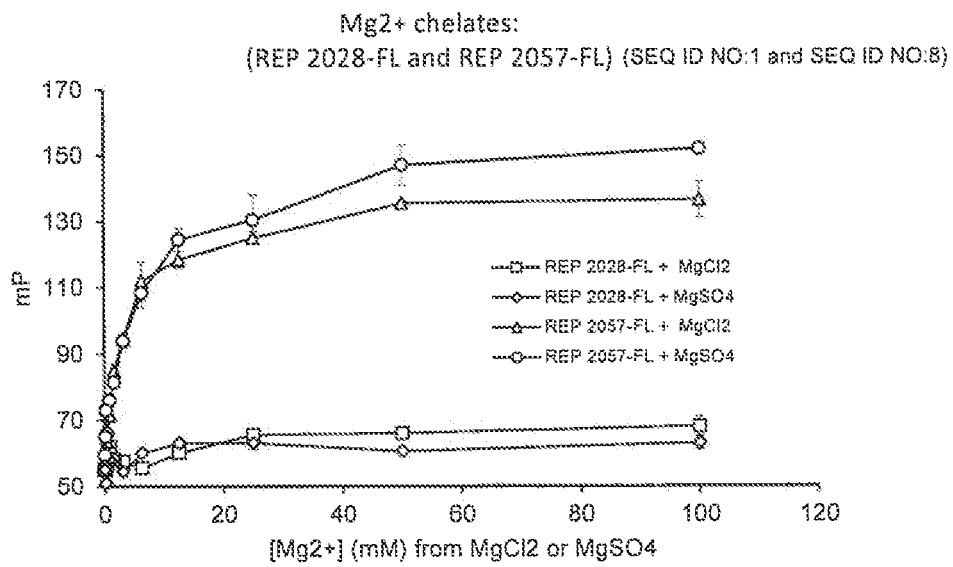
FIG. 22A) absence of ON chelate complex formation with REP 2028-FL (SEQ ID NO:11) and ON chelate complex formation REP 2057-FL (SEQ ID NO:8).
Figure 22B:
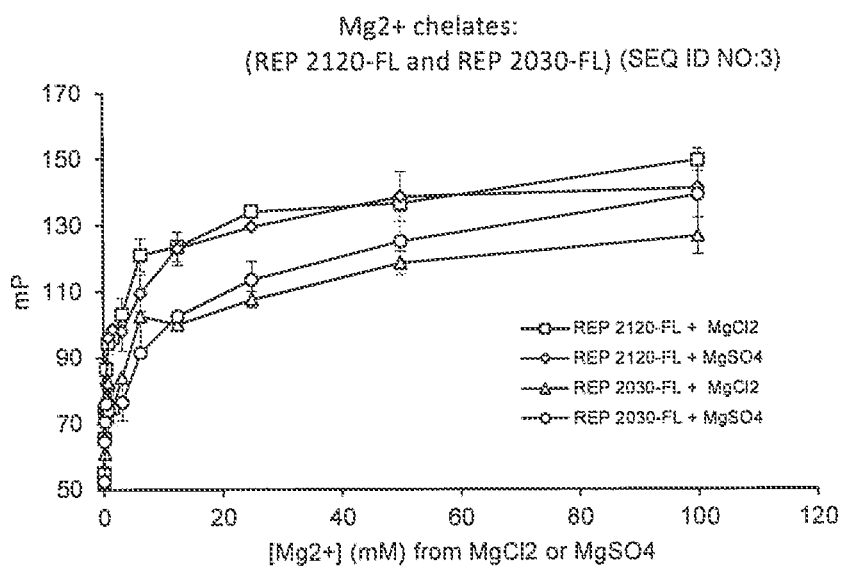
FIG. 22B) ON chelate complex formation with REP 2120-FL and REP 2030-FL (SEQ ID NO:3). Values represent average+/− standard deviation from duplicate measurements.
Figure 23A:
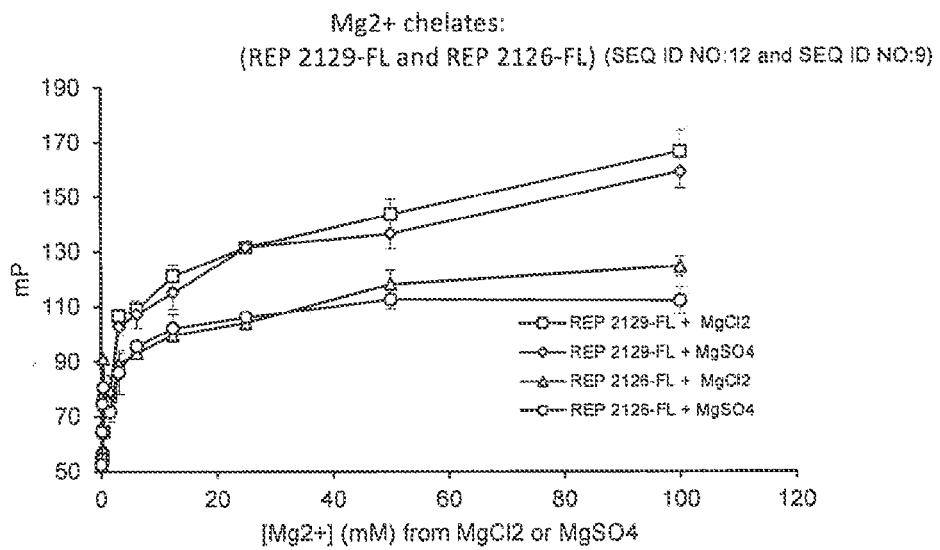
FIG. 23A) ON chelate complex formation with REP 2129-FL (SEQ ID NO:12) and REP 2126-FL (SEQ ID NO:9).
Figure 23B:
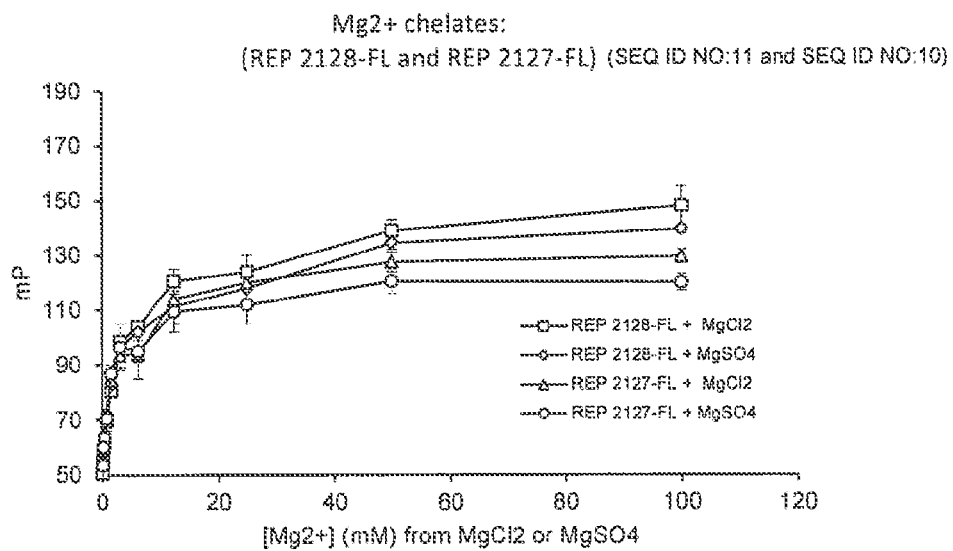
FIG. 23B) ON chelate complex formation with REP 2128-FL (SEQ ID NO:11) and REP 2127-FL (SEQ ID NO:10). Values represent average+/− standard deviation from duplicate measurements.
Figure 24A:
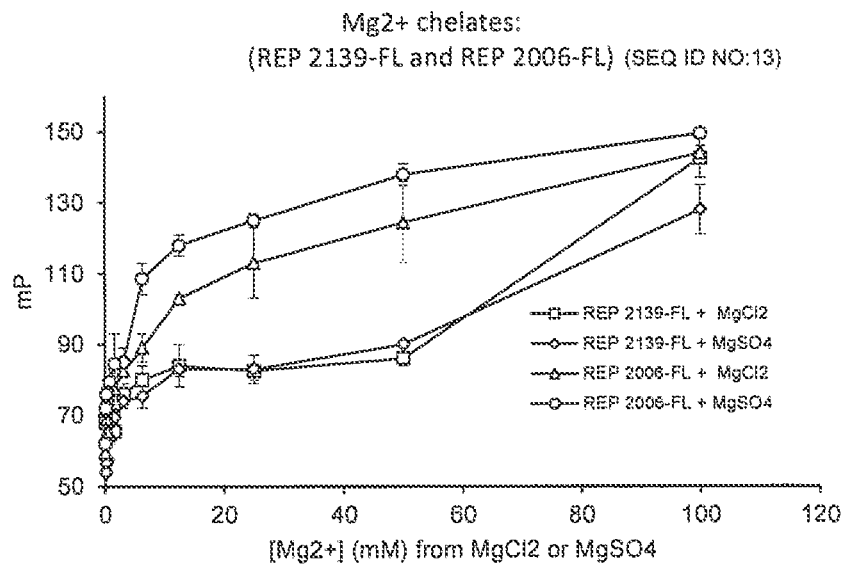
FIG. 24A) ON chelate with REP 2139-FL (SEQ ID NO:13) and REP 2006-FL.
Figure 24B:
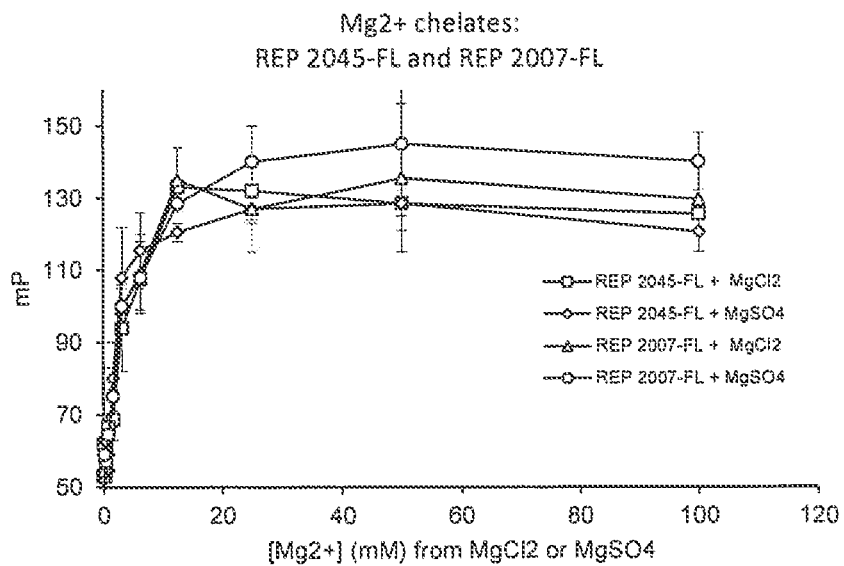
FIG. 24B) ON chelate complex formation with REP 2045-FL and REP 2007-FL. Values represent average+/− standard deviation from duplicate measurements.

N = degenerate sequence (random incorporation of A, G, C or T)
PS = phosphorothioation at each linkage
2' O Me = 2' O methylation at each ribose The 3' FITC labeled oligonucleotides used were REP 2032-FL (a 6 mer phosphorothioated degenerate oligodeoxynucleotide), REP 2003-FL (a 10mer phosphorothioated degenerate oligodeoxynucleotide), REP 2004-FL (a 20mer phosphorothioated degenerate oligodeoxynucleotide), REP 2006-FL (a 40mer phosphorothioated degenerate oligodeoxynucleotide), REP 2031-FL (a 40mer poly cytosine phosphorothioated oligodeoxynucleotide; SEQ ID NO:4), REP 2107-FL (a 40mer phosphorothioated degenerate oligonucleotide having each ribose modified by 2' O methyribose) and REP 2086-FL (a 40mer degenerate phosphodiester oligonucleotide having each ribose modified by 2' O methyribose). Each of these ONs was prepared as a 0.5 mM stock in 1 mM TRIS (pH 7.2). These stock were used to prepare 3 nM fluorescent ON solutions in FP buffer (10 mM TRIS, 80 mM NaCl, 1 mM EDTA, 10 mM β-mercaptoethanol and 0.1% Tween®-20). EDTA was present to remove any divalent metals present in the solution prior to FP measurements. Each of these buffer solutions also contained 80 mM NaCl to assess ON complex formation in the presence of a molar excess of monovalent cations (in each graph in FIGS. 1-12 this is reported as the 0 mM metal chloride concentration). To each fluorescent ON in solution was added various amounts of ACS grade chloride salts of divalent (2+) metals. These salts included calcium chloride, magnesium chloride, cobalt chloride, iron chloride, manganese chloride, barium chloride, nickel chloride, copper chloride, zinc chloride, cadmium chloride, mercury chloride and lead chloride. The formation of dimers or higher order ON chelate complexes was monitored by an increase in fluorescence polarization (quantified by the dimensionless unit "mP") so that increased formation of ON chelate complexes resulted in larger changes in mass. The resulting slower tumbling of these ON chelate complexes in solution leads to increased polarization of emitted fluorescence (see FIG. 16). The results of these experiments are presented in FIGS. 2-13. In each case, significant increases in fluorescence polarization were seen with all ONs in the presence of all divalent cations but not in the presence of high molar excess of Na+ (supplied as NaCl), indicating the formation of ON chelate complexes with divalent metal cations only. These results demonstrate the following:

- ONs in the presence of 80 mM NaCl do not exhibit any detectable formation of dimers or any other higher order ON complexes.
- ONs form dimers and higher order complexes in the presence of the following divalent metal cations when they exist in the 2+ charge state: calcium, magnesium, cobalt, iron, manganese, barium, nickel, copper, zinc, cadmium, mercury and lead. The formation of these ON complexes involves the interaction of ONs with these divalent metal cations.
- The formation of ON complexes cannot be due to hybridization between nitrogenous bases vial traditional Watson-Crick interactions due to the degenerate nature of the ONs tested. Additionally, REP 2031 (SEQ ID NO:4) cannot self-hybridize under the experimental conditions employed.
- The formation of ON complexes is stable and soluble in aqueous solution and since these complexes appear to incorporate the divalent metal in question as part of the complex formed, these ON complexes have the effect of chelating the divalent metal in question from the solution in which the ON complex was formed.
- Chelation of these metals and formation of the ON chelate complex is not dependent on a particular nucleotide sequence, as evidenced by the chelation observed with degenerate oligonucleotides and also not dependent on nucleotide modifications involving modification of the phosphodiester linkage or the 2' ribose moiety.

Chelation of these metals occurs with oligonucleotides from 6-40 nucleotides in length.

Chelation of these metals occurs in the presence or absence of phosphorothioation or 2' ribose modification.

The expansive formation of ON chelate complexes with numerous divalent metal cations with all ONs in this example also strongly suggests the following:

Because divalent cations catalyze ON complex formation and monovalent cations do not, and because ON complex formation is not occurring via base hybridization as described above, ON chelate complex formation must involve some form of "metal ion bridge" between two ONs at locations which easily share an electron capable of filling an empty electron orbital in the cation. The locations most amenable to this "electron sharing" are the non-bridging oxygen (or sulfur in the case of phosphorothioation) atoms in the phosphodiester linkage (see FIG. 14B).

Double stranded ONs, whether DNA or RNA are expected to exhibit the same chelate complex formation and thus have the same propensity to chelate metal cations from solution.

Figure 15:
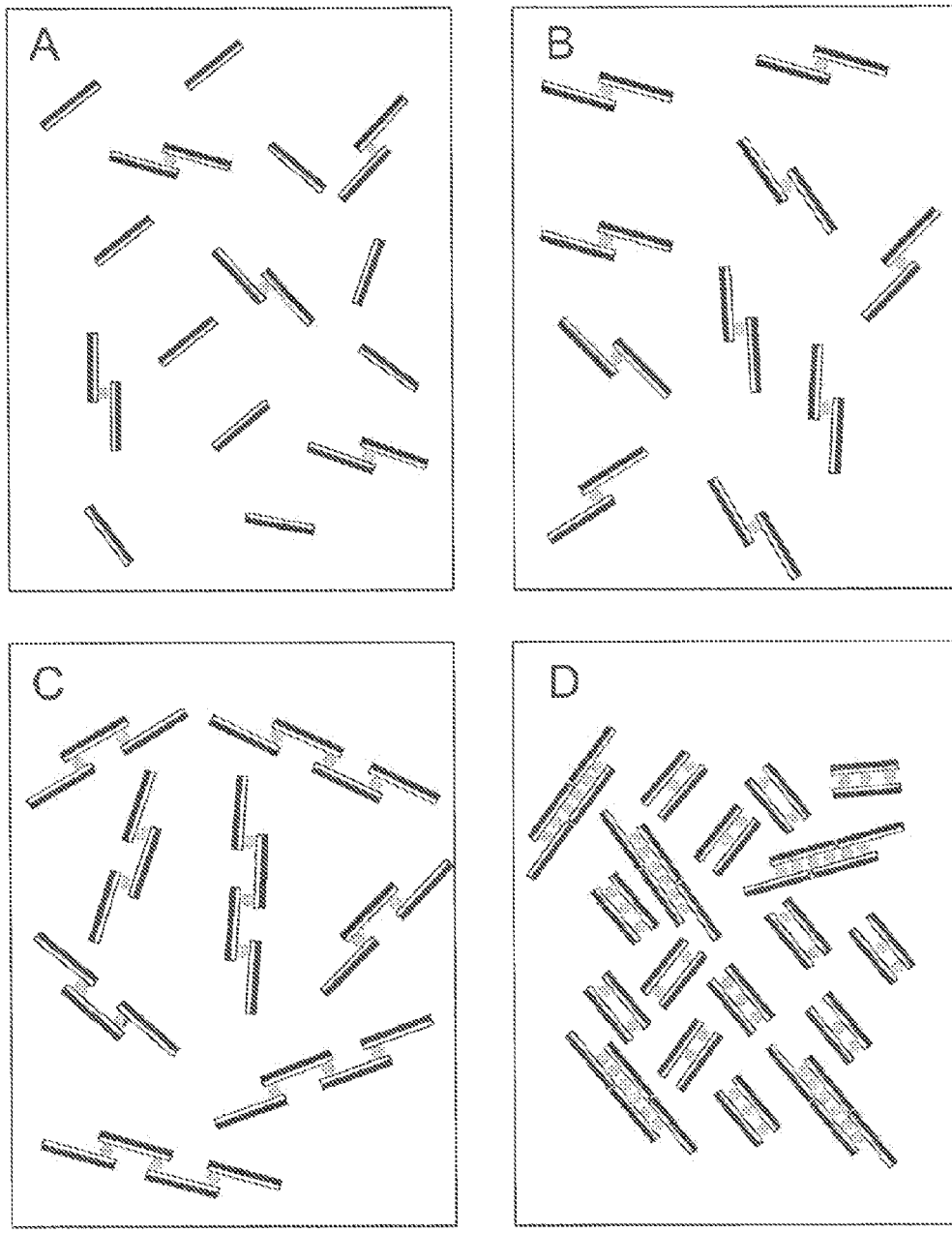
FIG. 15 illustrates the model for solution behavior of ONs in the presence of divalent metal cations at varying ON and divalent metal cation concentrations. A) Low divalent/trivalent metal cation, low ON concentrations yield dimers or low order ON chelate complexes. B) Increasing divalent/trivalent metal cation concentrations yield more complete ON chelate complex formation in the solution. C) Further increasing ON concentrations in the presence of divalent or trivalent metals are capable of yielding higher order ON chelate complexes with increasing metal concentrations. All the chelate complexes in (A) through (C) are soluble in aqueous solution by virtue of having hydrophilic surfaces still exposed to the aqueous environment thus maintaining solubility. D) At sufficient ON and metal concentration, all hydrophilic surfaces are now constrained within the ON chelate complexes, leaving only the hydrophobic surfaces exposed to the aqueous environment. This results in precipitation of the ON chelate complex.

These metal bridges must involve intermolecular interactions as intramolecular interactions would not result in any significantly increased fluorescence polarization (see FIGS. 15 A-C and 16).

Soluble ON chelate complexes exist at any concentration of ONs and divalent cations which does not form chelate complex precipitates.

ONs cannot form salts with divalent metal cations and do not behave as salts in aqueous solution. This is in contrast to monovalent cations (exemplified by sodium in this example but also applicable to other monovalent cations such as potassium, lithium or ammonium) which do form salts with ONs and behave as salts (electrolytes) in solution. Moreover, although all ONs used in this example were ammonium salts, in aqueous solution, the ammonium ion likely dissociates from the ON (as would be expected of a salt) and provides no inhibition for the formation of ON chelate complexes by divalent cations. This is further strengthened by the observation that additional monovalent salt (in this case 80 mM NaCl) does not appear to interfere with the formation of ON chelate complexes with divalent cations.

That the formation of ON chelate complexes can be expected to occur with any metal, transition metal, lanthanide or actinide element with a 2+ charge state and is also likely to occur with metal ions which can exist in a 3+ or higher charge state (e.g. chromium).

That ONs greater than 40mer in length or harboring other modifications or having any particular defined nucleotide sequence can also be expected to form ON chelate complexes with divalent metal cations so long as they contain linkages which are capable of sharing electrons in the same fashion as non-bridging oxygen (or sulfur) atoms in traditional phosphodiester linkages.

ON salts (e.g. sodium salts) may be useful to chelate divalent metals within a human or non-human patient such as but not limited to: cadmium, mercury, lead. Additionally, chelation of any one particular divalent metal cation (e.g. iron) by a sodium salt oligonucleotide may be suppressed by preparing the ON sodium salt as an ON chelate complex with another divalent metal cation (e.g. calcium).

Metal salts other than chloride salts may also permit the formation of ON chelate complexes. Taking calcium salts as an example, other calcium salts compatible with ON chelate complex formation may include without restriction calcium gluconate, calcium citrate, calcium lactate, calcium malate, calcium aspartate, calcium fumarate, calcium ascorbate, calcium benzoate, calcium erythorbate, and/or calcium propionate.

EXAMPLE III

ONs Form Chelate Complexes with Different Salts of Calcium and Magnesium

In order to further demonstrate the universal nature of ON chelate complex formation and to also demonstrate the utility of different salts of divalent metal cations in the formation of ON chelate complexes, two different forms of calcium and magnesium salts were used to prepare diverse ON chelate complexes with ONs of different specific sequences. The salts used were calcium chloride, calcium sulfate, magnesium chloride and magnesium sulfate. The ONs used are listed in Table 2 below. FP reaction conditions were identical to those in Example 1 except that EDTA was omitted to demonstrate the formation of ON chelate complexes in the absence of any EDTA-mediated effects.

TABLE 2

ONs used in Example III

| Oligonucleotide | Sequence (5'-3') | SEQ. ID NO. | Modifications |
|---|---|---|---|
| REP 2055-FL | $(AC)_{20}$ | 6 | PS |
| REP 2056-FL | $(TC)_{20}$ | 7 | PS |
| REP 2033-FL | $(TG)_{20}$ | 5 | PS |
| REP 2029-FL | $A_{40}$ | 2 | PS |
| REP 2028-FL | $G_{40}$ | 1 | PS |
| REP 2057-FL | $(AG)_{20}$ | 8 | PS |
| REP 2120-FL | $N_{40}$ (C = 5' methylcytidine) | NA | PS |
| REP 2030-FL | $T_{40}$ | 3 | PS |
| REP 2129-FL | $C_{60}$ | 12 | PS |
| REP 2126-FL | $C_{20}$ | 9 | PS |
| REP 2128-FL | $C_{50}$ | 11 | PS |
| REP 2127-FL | $C_{30}$ | 10 | PS |
| REP 2006-FL | $N_{40}$ | NA | PS |
| REP 2139-FL | $(A5'MeC)_{20}$ | 13 | PS + 2' O Me |
| REP 2045-FL | $N_{60}$ | NA | PS |
| REP 2007-FL | $N_{80}$ | NA | PS |

N = degenerate sequence (random incorporation of A, G, C or T)
PS = phosphorothioation at each linkage
2' O Me = 2' O methylation at each ribose
NA = not applicable (sequence is degenerate)

The results of these experiments are illustrated in FIGS. 17-24 and demonstrate that all ONs tested can form ON complexes with different salts of calcium and magnesium. Two exceptions to this general observation are REP 2028-FL (40mer poly G, SEQ ID NO:1; FIGS. 18A and 22A) and REP 2029-FL (40mer poly A, SEQ ID NO:2; FIGS. 17B and 21B). Both of these ONs are polypurines and, especially in the case of poly G, are known to form thermodynamically stable intramolecular interactions (termed "G-quartets" in the case of poly G tracts) which result in these ONs forming tight intramolecular complexes where the phosphodiester backbone is likely partially folded within this complex or no longer able to participate in solution interactions (like chelate complex formation. REP 2029-FL (SEQ ID NO:2) was weakly able to form chelate complexes which is likely due to the weak "A-quartet" interactions occurring with this ON.

Thus, not encompassed herein are ONs which only comprise poly A and poly G and aptamers which form thermodynamically stable intramolecular interactions. The ONs encompassed herein are not fully poly A or poly G ONs and/or haptamers.

The results from Example II show that different salt forms of magnesium and calcium can be used to prepare ON chelate complexes and further illustrate the following:

All ONs in Example II (except REP 2006-FL) contain specific sequences which do not contain any palindromic sequences capable of forming hairpins neither are any of these sequences self-complimentary. Therefore, none of the ON chelate complex formations observed are attributable to hybridization events.

The poor ability of REP 2028-FL (SEQ ID NO:1) and REP 2029-FL (SEQ ID NO:2) to form ON chelate complexes suggests that a relaxed phosphodiester backbone is required for ON chelate complex formation again pointing to the phosphodiester backbone as the chemical feature on ONs required for the linking of two or more ONs to form chelate complexes.

Any ON which contains a phosphodiester backbone is expected be able to form chelate complexes, regardless of other existing modifications such as phosphorothioation, 2' ribose modification or locked nucleic acid modification.

ON chelate complexes can be formed with ONs as large as 80mer in length and ONs greater than 80mer length also exhibit the same behavior in the presence of divalent metal cations.

EXAMPLE IV

Formation of ON Chelate Complexes with Double Stranded ONs

Figure 25:
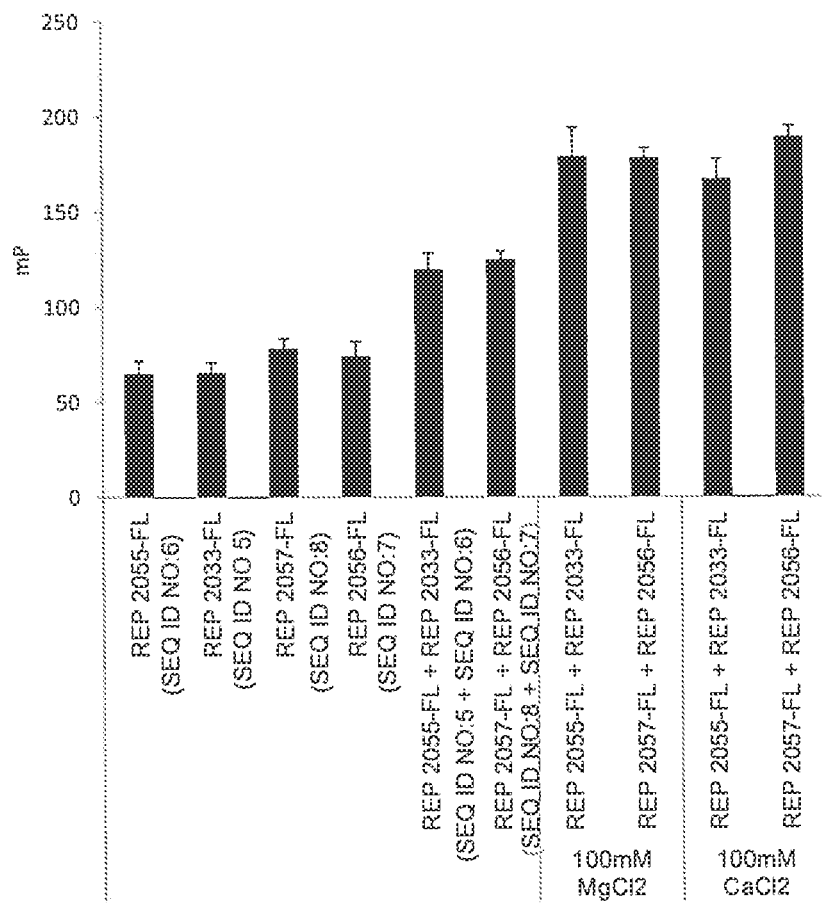
FIG. 25 shows the formation of two different double stranded ON chelate complexes in the presence of calcium chloride or magnesium chloride as measured by fluorescence polarization. The double stranded ONs were prepared by hybridization of REP 2055-FL (SEQ ID NO:6) with REP 2033-FL (SEQ ID NO:5) and REP 2057-FL (SEQ ID NO:8) with REP 2056-FL (SEQ ID NO:7). Values represent average+/− standard deviation from triplicate measurements.

Double stranded oligonucleotides are formed from two single stranded complementary oligonucleotides which in aqueous solution hybridize to each other via Watson-Crick interactions. Since double stranded ONs still have a phosphodiester backbone exposed on the outside of the DNA helix formed, they should be able to form chelate complexes in the presence of divalent cations. In order to test this hypothesis, two different double stranded DNA oligonucleotides were prepared by hybridizing REP 2055-FL (40mer poly AC; SEQ ID NO:6) with REP 2033-FL (40mer poly TG; SEQ ID NO:5) and REP 2057-FL (40mer poly AG; SEQ ID NO:8) with REP 2056-FL (40mer poly TC; SEQ ID NO:7). Because ON hybridization results in a duplex, the resulting increase in mass can be detected by an increase in fluorescence polarization relative to the single stranded ONs used to prepare the complex. Single stranded ONs (REP 2055-FL (SEQ ID NO:6), Rep 2033-FL (SEQ ID NO:5), Rep 2057-FL (SEQ ID NO:8) and REP 2056-FL (SEQ ID NO:7)) were each diluted to 20 nM in 1×FP buffer. The hybridization of the two complementary pairs as identified above were also carried out in 1×FP buffer (10 nM of each ON) and hybridization was confirmed by an increase in fluorescence polarization. The double stranded constructs were then exposed to 100 mM $CaCl_2$ or 100 mM $MgCl_2$. On chelate complex formation was monitored by a further increase in fluorescence polarization (see FIG. 25). The results of this experiment confirm the successful hybridization of both complimentary pairs of ONs into double stranded ONs as evidenced by the increase in fluorescence polarization. Moreover, the addition of either $CaCl_2$ or $MgCl_2$ to these double stranded ONs resulted in a further increase in fluorescence polarization, indicating that these double stranded ONs could also form chelate complexes in the presence of divalent metal cations. These results also strongly suggest that double stranded ONs can form ON chelate complexes with any divalent cation and would also be expected to have the effect of sequestering said divalent cations from solution.

EXAMPLE V

Diverse Monovalent Cations do not Form Chelate Complexes with ONs

Figure 26:
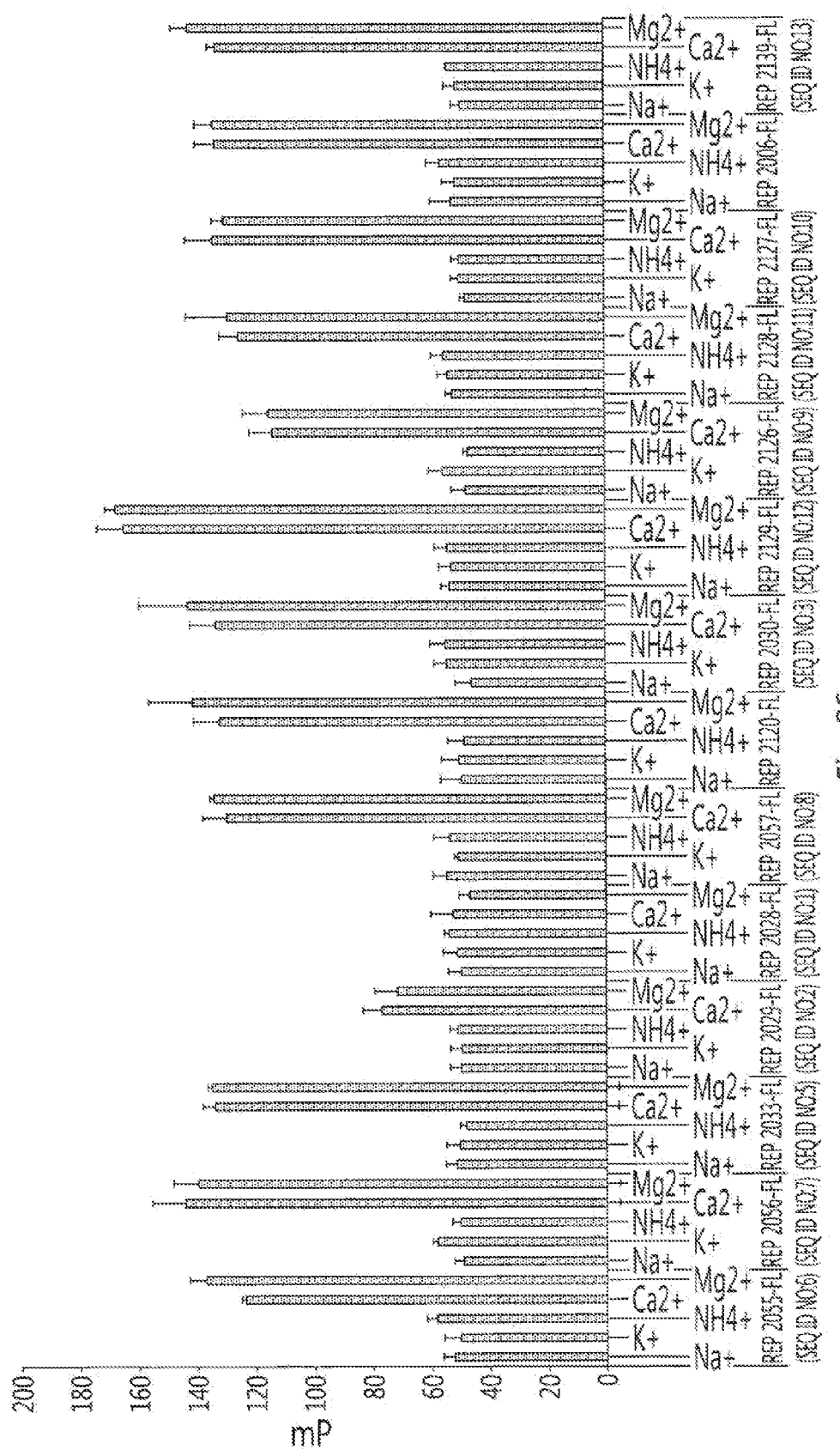
FIG. 26 shows the formation of diverse ON chelate complexes only in the presence of divalent metal cations ($Mg^{2+}$ and $Ca^{2+}$) and not in the presence of monovalent cations ($Na^+$, $K^+$ or $NH_4^+$). Values represent average+/− standard deviation from triplicate measurements.

In order to more specifically demonstrate that the formation of ON chelate complexes cannot occur in the presence of monovalent cations and specifically require divalent cations for their formation, ON complex formation with many ONs (see Example 2) was observed in FP buffer which contained only once source of cation. 1× FP buffer was prepared containing only one of the following salts: sodium chloride, potassium chloride, ammonium chloride, calcium chloride or magnesium chloride, all at 80 mM concentration so that the concentration of cations in the FP buffer was equivalent. Fluorescently labeled ONs as described in Example 2 were diluted to 10 nM in the different FP buffers and ON chelate complex formation was monitored by fluorescence polarization (see FIG. 26). In the case of each ON tested, chelate complex formation was observed only with the cations $Mg^{2+}$ and $Ca^{2+}$ and not with any of the monovalent cations tested ($Na^+$, $K^+$ or $NH_4^+$). As observed in Example III, REP 2029-FL (SEQ ID NO:2) and REP 2028-FL (SEQ ID NO:1) displayed only moderate or no complex formation, respectively in the presence of calcium or magnesium. This further confirms that ONs can only form chelate complexes with divalent cations whereas ONs can only exist as salts with monovalent salts.

EXAMPLE VI

Evaluation of metal content in On chelate complexes prepared in Wfi

To demonstrate the broad applicability of ON chelate complex preparation to all ONs, several different ON chelate complexes were prepared using the ONs and $^{2+}$metal chloride salts as indicated in Table 3. All ONs used in these preparations were sodium salts which had been desalted to remove sodium derived from NaCl and leave only sodium integral to ON salt formation in the final lyophilized ON. ON chelate complexes were prepared in water for injection (WFI) by first dissolving the proscribed amount of ON sodium salt to 50 mg/ml concentration and adding the proscribed amount of divalent metal chloride salt to the ON solution. ON solutions prior to divalent metal chloride addition/ON chelate formation were analyzed for sodium and the relevant metal by inductively coupled plasma-optical emission spectroscopy (ICP-OES). After ON chelate complex formation, samples were desalted by ultrafiltration using a 5000 MWCO regenerated cellulose filter. This filter has previously been validated to allow the permeation of free salts but not ONs or cations attached to ONs. The retentate solution (containing ON chelate complexes) was analyzed for sodium and metal content by ICP-OES and for chloride content by ion chromatography to confirm that the divalent metals present were chelated on ONs and not derived from divalent metal salts present in the retentate solution (Table 4).

TABLE 3

Preparation of diverse ON chelate complexes

| ON | Sequence/chemistry | Metal Chelate Prepared | Metal chloride added (mg/100 mg of ON) | ON concentration |
|---|---|---|---|---|
| REP 2004 | $N_{20}$/PS | Ca | 10 | 50 mg/ml |
| REP 2006 | $N_{40}$/PS | Ca | 10 | 50 mg/ml |
| REP 2006 | $N_{40}$/PS | Ca | 20 | 50 mg/ml |
| REP 2006 | $N_{40}$/PS | Ca | 30 | 25 mg/ml |
| REP 2006 | $N_{40}$/PS | Mg | 20 | 50 mg/ml |
| REP 2006 | $N_{40}$/PS | $Fe^{2+}$ | 2 | 25 mg/ml |
| REP 2107 | $N_{40}$/PS, 2'OMe | Ca | 10 | 37.5 mg/ml |
| REP 2107 | $N_{40}$/PS, 2'OMe | Mg | 15 | 37.5 mg/ml |
| REP 2107 | $N_{40}$/PS, 2'OMe | $Fe^{2+}$ | 2 | 37.5 mg/ml |
| REP 2138 | $C_{40}$/2'OMe | Ca | 10 | 50 mg/ml |
| REP 2126 (SEQ ID NO: 9) | $C_{20}$/PS | Ca | 10 | 50 mg/ml |
| REP 2031 (SEQ ID NO: 4) | $C_{40}$/PS | Ca | 10 | 50 mg/ml |
| REP 2129 (SEQ ID NO: 12) | $C_{60}$/PS | Ca | 10 | 50 mg/ml |
| REP 2057 (SEQ ID NO: 8) | $(AG)_{20}$/PS | Ca | 10 | 50 mg/ml |
| REP 2057 (SEQ ID NO: 8) | $(AG)_{20}$/PS | Mg | 15 | 50 mg/ml |
| REP 2057 (SEQ ID NO: 8) | $(AG)_{20}$/PS | $Fe^{2+}$ | 2 | 50 mg/ml |
| REP 2055 (SEQ ID NO: 6) | $(AC)_{20}$/PS | Ca | 10 | 50 mg/ml |
| REP 2139 (SEQ ID NO: 13) | $(A,5MeC)_{20}$/PS,2'OMe | Ca | 10 | 50 mg/ml |
| REP 2139 (SEQ ID NO: 13) | $(A,5MeC)_{20}$/PS,2'OMe | Ca | 30 | 25 mg/ml |
| REP 2139 (SEQ ID NO: 13) | $(A,5MeC)_{20}$/PS,2'OMe | Mg | 15 | 50 mg/ml |
| REP 2139 (SEQ ID NO: 13) | $(A,5MeC)_{20}$/PS,2'OMe | Ca, Mg | 5/7.5 | 50 mg/ml |

N = degenerate base (being a random distribution of A, G, T or C)
PS = phosphorothioate
2'OMe = 2' O methylated ribose
5MeC = 5'methylcytidine

TABLE 4

Validation of metal content in diverse ON chelate complex solutions

| ON | Metal Chelate (mg/100 mg ON) | Pre-chelate ON solution | | Post-desalting ON chelate complex | | |
|---|---|---|---|---|---|---|
| | | sodium | metal | chloride | sodium | metal |
| REP 2004 | Ca (10) | 0.276% | <2.0 ppm | <10 ppm | <0.03% | 664 ppm |
| REP 2006 | Ca (10) | 0.381% | <11 ppm | <8 ppm | 400 ppm | 614 ppm |
| REP 2006 | Ca (20) | 0.443% | 1.21 ppm | <8 ppm | 141 ppm | 0.11% |
| REP 2006 | Ca (30) | 0.399% | 2.0 ppm | <8 ppm | <110 ppm | 861 ppm |
| REP 2006 | Mg (20) | 0.390% | <5 ppm | <9 ppm | 110 ppm | 564 ppm |
| REP 2006 | $Fe^{2+}$ (2) | 0.394% | <5 ppm | <10 ppm | 979 ppm | 176 ppm |
| REP 2107 | Ca (10) | 0.232% | <6 ppm | <9 ppm | 215 ppm | 539 ppm |
| REP 2107 | Mg (15) | 0.237% | <0.9 ppm | <9 ppm | 162 ppm | 339 ppm |
| REP 2107 | $Fe^{2+}$ (2) | 0.219% | 2.5 ppm | 15 ppm | 0.049% | 141 ppm |
| REP 2138 | Ca (10) | 0.210% | <0.04% | <10 ppm | 3.2 ppm | 745 ppm |
| REP 2126 (SEQ ID NO: 9) | Ca (10) | 0.266% | <2.3 ppm | <10 ppm | <0.04% | 681 ppm |
| REP 2031 (SEQ ID NO: 4) | Ca (10) | 0.222% | <2.4 ppm | <9 ppm | <0.03% | 772 ppm |
| REP 2129 (SEQ ID NO: 12) | Ca (10) | 0.236% | <2.4 ppm | <10 ppm | <0.03% | 681 ppm |
| REP 2057 (SEQ ID NO: 8) | Ca (10) | 0.257% | 5.5 ppm | <10 ppm | 398 ppm | 743 ppm |
| REP 2057 (SEQ ID NO: 8) | Mg (15) | 0.250% | <1 ppm | <9 ppm | 177 ppm | 531 ppm |
| REP 2057 (SEQ ID NO: 8) | $Fe^{2+}$ (2) | 0.244% | 0.7 ppm | <9 ppm | 0.101% | 195 ppm |

TABLE 4-continued

Validation of metal content in diverse ON chelate complex solutions

| ON | Metal Chelate (mg/100 mg ON) | Pre-chelate ON solution | | Post-desalting ON chelate complex | | |
|---|---|---|---|---|---|---|
| | | sodium | metal | chloride | sodium | metal |
| REP 2055 (SEQ ID NO: 6) | Ca (10) | 0.238% | <6 ppm | <9 ppm | 351 ppm | 639 ppm |
| REP 2139 (SEQ ID NO: 13) | Ca (10) | 0.244% | <6 ppm | <8 ppm | 347 ppm | 638 ppm |
| REP 2139 (SEQ ID NO: 13) | Ca (30) | 0.236% | <1.8 ppm | <8 ppm | 91 ppm | 937 ppm |
| REP 2139 (SEQ ID NO: 13) | Mg (15) | 0.247% | <1 ppm | <9 ppm | 248 ppm | 472 ppm |
| REP 2139 (SEQ ID NO: 13) | Ca (5), Mg (7.5) | 0.276% | <9 ppm (ca) <5 ppm (Mg) | <10 ppm | 0.022% | 0.033% (Ca) 0.314% (Mg) |

These results confirm the partial displacement of sodium by calcium, magnesium or iron (2+) in ONs varying in length from 20-60mer, varying in sequence from fully degenerate ONs to three specific sequences (poly C, poly AC and poly AG) and in ONs with or without phosphorothioate modifications, with or without 2' ribose modifications and containing phosphorothioate and 2' ribose modifications. The ability to formulate 2'O methyl ribose modified ONs as chelate complexes is expected to also extend to ONs containing any other 2' ribose modification such as but not restricted to 2' fluoro and 2' O methyribose. Further, they demonstrate that significant sodium displacement is achieved with minimal increased in divalent metal content, consistent with the ON chelate complex structures described in FIG. 15. These results also illustrate the various combinations of calcium, magnesium, iron (2+) and mixed calcium/magnesium salt solutions which can be used to prepare ON chelate complexes and show that any divalent metal salt solution or mixture of divalent metal salt solutions could be similarly used to prepare ON chelate complexes.

Therefore, ON chelate complexes can be prepared from ONs which are fully phosphorothioated or not, containing any number of phosphorothioated linkages, containing at least one 2' ribose modification or fully 2' ribose modified or containing no 2' ribose modification. ONs can be RNA or DNA or a hybrid containing RNA and DNA. The metal salt used in the preparation of an ON chelate complex includes without restriction a calcium salt, a magnesium salt, an iron salt, any other divalent metal salt.

EXAMPLE VII

Preparation of Stable ON Chelate Complexes in Normal Saline

Having demonstrated the broadly conserved nature of ON chelate complex formation and preparation with different divalent metals in Examples II and III, the preparation of stable, soluble ON calcium chelate complexes was examined in normal saline, a more appropriate excipient for ON chelate complex administration to a subject. For this experiment, a 200 mg/ml solution of the sodium salt of REP 2006 in normal saline was used as the source of ON. The source of calcium was a 10% solution of $CaCl_2$ in WFI (100 mg/ml $CaCl_2$). Various REP 2006 calcium chelate complexes using different calcium and REP 2006 concentrations were prepared in 1 ml solutions at room temperature (see Table 5) according to the following protocol: 1) add REP 2006 to the vial, 2) add normal saline and mix and 3) add $CaCl_2$ and mix. These REP 2006 calcium chelate solutions were observed for the appearance of precipitate over 36 days (see Table 6).

TABLE 5

Conditions for the preparation of various REP 2006 calcium chelate complexes.

| [REP2006] (mg/ml) | $CaCl_2$ (mg per 100 mg of REP 2006) | | | | | |
|---|---|---|---|---|---|---|
| | 15 | 20 | 25 | 30 | 35 | 40 |
| 100 | 500 ul REP 2006 + 350 ul NS + 150 ul $CaCl_2$ | 500 ul REP 2006 + 300 ul NS + 200 ul $CaCl_2$ | 500 ul REP 2006 + 250 ul NS + 250 ul $CaCl_2$ | 500 ul REP 2006 + 200 ul NS + 300 ul $CaCl_2$ | 500 ul REP 2006 + 150 ul NS + 350 ul $CaCl_2$ | 500 ul REP 2006 + 100 ul NS + 400 ul $CaCl_2$ |
| 50 | 250 ul REP 2006 + 675 ul NS + 75 ul $CaCl_2$ | 250 ul REP 2006 + 650 ul NS + 100 ul $CaCl_2$ | 250 ul REP 2006 + 625 ul NS + 125 ul $CaCl_2$ | 250 ul REP 2006 + 600 ul NS + 150 ul $CaCl_2$ | 250 ul REP 2006 + 575 ul NS + 175 ul $CaCl_2$ | 250 ul REP 2006 + 550 ul NS + 200 ul $CaCl_2$ |
| 25 | 125 ul REP 2006 + 837.5 ul NS + 37.5 ul $CaCl_2$ | 125 ul REP 2006 + 825 ul NS + 50 ul $CaCl_2$ | 125 ul REP 2006 + 812.5 ul NS + 62.5 ul $CaCl_2$ | 125 ul REP 2006 + 800 ul NS + 75 ul $CaCl_2$ | 125 ul REP 2006 + 787.5 ul NS + 87.5 ul $CaCl_2$ | 125 ul REP 2006 + 775 ul NS + 100 ul $CaCl_2$ |

TABLE 6

Formation of precipitate in REP 2006 calcium chelate complexes at various ON and calcium concentrations

| TIME | [REP 2006] (mg/ml) | CaCl₂ (mg per 100 mg of NAP) | | | | | |
|---|---|---|---|---|---|---|---|
| | | 15 | 20 | 25 | 30 | 35 | 40 |
| 1 h | 100 | − | + | ++ | +++ | +++ | ++++ |
| | 50 | − | − | − | − | − | + |
| | 25 | − | − | − | − | − | − |
| 24 h | 100 | − | −/+ | +++++ | +++++ | +++++ | +++++ |
| | 50 | − | − | − | − | + | +++++ |
| | 25 | − | − | − | − | − | − |
| 7 d | 100 | − | −/+ | +++++ | +++++ | +++++ | +++++ |
| | 50 | − | − | − | − | +++++ | +++++ |
| | 25 | − | − | − | − | − | − |
| 36 d | 100 | −/+ | −/+ | +++++ | +++++ | +++++ | +++++ |
| | 50 | −/+ | −/+ | −/+ | −/+ | +++++ | +++++ |
| | 25 | − | − | − | − | − | − |

− clear, transparent solution
+ very small amount of white precipitate at bottom of vial
++ fine colloidal precipitate, translucent
+++ fine colloidal precipitate, opaque
++++ precipitate primarily at bottom of tube but residual colloids present
+++++ precipitate at bottom of tube, remaining solution is clear and transparent In all cases, the solutions of REP 2006 calcium chelates demonstrated reduced surface tension and increased viscosity in comparison to REP 2006 solutions in the absence of calcium (at all concentrations tested), as evidenced by a more pronounced meniscus in the vial and in the viscous solution behavior when vials were gently inverted. This solution behavior is consistent with the formation of large soluble multimeric complexes (chelate complexes) as depicted in FIGS. 15 A-C. Even in those vials where precipitate had formed, the remaining solution still displayed this characteristic increase in surface tension and viscosity. It is possible that the precipitates formed in these solutions had adopted the saturated (and insoluble) ON chelate structures as illustrated in FIG. 15D with the residual unprecipitated ON and calcium still forming soluble chelates in the solution. These behaviors are expected to be generally representative of the behavior of any ON chelate complex, regardless of ON length, chemistry, structure (single stranded or double stranded) or divalent metal present. Moreover, these experiments also demonstrate that while higher concentrations of ON and calcium may initially form completely soluble complexes, these are likely to be dynamically unstable and slowly transition from soluble chelate complexes (as in FIGS. 15 A-C) to insoluble chelate complexes (FIG. 15D). Thus it may be desirable to prepare ON chelate complexes at ON and metal concentrations such as those shown in Table 5 which have soluble ON chelate complexes which are stable in solution. For different ONs and metal combinations, the optimal ON and metal concentrations resulting in soluble ON chelate complexes which remain soluble in solution over time may vary from those concentrations shown for REP 2006 and calcium in Table 5.

Examples VI and VII describe various combinations of ON and divalent metal salt concentrations in different excipients which can be useful in the preparation of ON chelate complexes and describes combinations of ON and divalent metal salts or mixtures of divalent metal salts which result in ON chelate complex solutions which in normal saline either precipitate rapidly, precipitate slowly or remain fully soluble over an extended period of time. It may be advantageous to use ON chelate solutions with any of these stability characteristics.

Therefore, ON chelate complexes can be prepared using any ON salt including but not restricted to an ON sodium salt or an ON ammonium salt or a mixed sodium/ammonium ON salt. Ideally, the ON salt is dissolved in aqueous excipient including but not restricted to water for injection or normal saline. The source of divalent metal to be used for ON chelate formation can be a chloride salt, a sulfate salt or any other pharmaceutically acceptable salt including but not restricted to a gluconate salt, a citrate salt, a lactate salt, a malate salt, an aspartate salt, a fumarate salt, an ascorbate salt, a benzoate salt, an erythorbate salt, and/or a propionate salt. The salt can comprise any of the following divalent metal cations: calcium, magnesium, iron (2+), manganese, copper and/or zinc. Additionally, a mixture of more than one metal salt can be used. Said metal salt can be used directly in powder form but is preferably prepared as an aqueous solution in the same excipient as the ON is dissolved in. The metal salts can be prepared at any concentration to the limit of solubility for said metal salt in said excipient. ON chelate complexes are preferably prepared by slowly adding the metal salt solution to the ON solution with constant mixing to prevent the accumulation of ON chelate precipitates during the addition of the salt solution. Depending on the concentration of ON and metal salt used, ON chelate solutions may slowly form ON chelate precipitates over time or remain completely soluble (see Example VII).

EXAMPLE VIII

Chelation of Serum Calcium by Ons Causes Anti-coagulation of Blood

Figure 27:
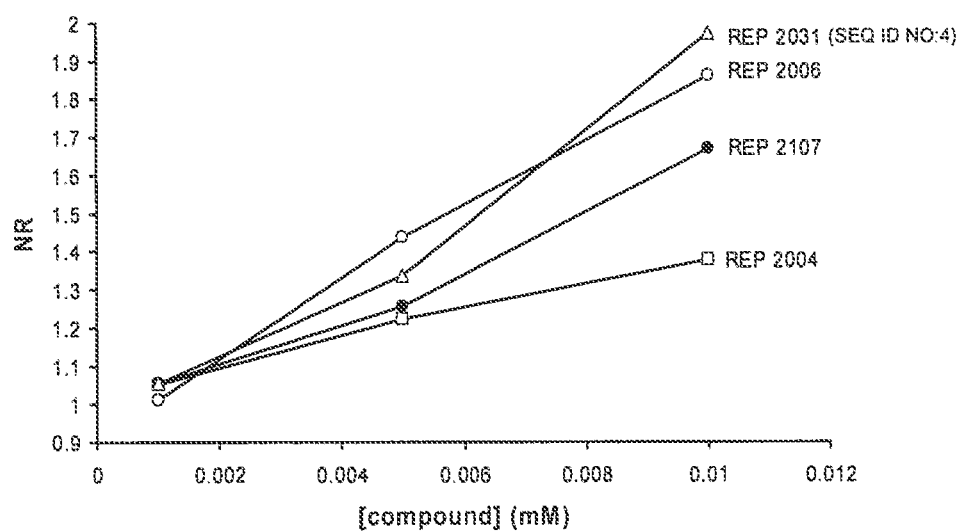
FIG. 27 shows the anti-coagulation effect of the addition of various concentrations of ONs of different sizes (REP 2004, REP 2006) and different chemistries (REP 2006, REP 2107) to human blood. The non-sequence dependent manner of this interaction was demonstrated by using degenerate oligonucleotides (REP 2004, REP 2006, REP 2107) but was also demonstrated using a sequence specific oligonucleotide (REP 2031; SEQ ID NO:4). Blood anti-coagulation in the presence of these compounds was monitored by measuring pro-thrombin time (PTT) and comparing it to PTT in the presence of normal saline in the blood using accepted clinical laboratory test methodologies. The ratio of PTT in the presence and absence of drug yields the normalized ratio (NR). A NR of 1 indicates normal blood coagulation activity and a NR above 1 indicates blood coagulation activity has been impaired (anti-coagulation).

The anti-coagulation effects of specific ONs have been previously described but to demonstrate the anti-coagulation effects of the ONs chelate complexes in the present disclosure, non FITC labeled ONs were prepared as high purity sodium salts so as to be biologically compatible. These ONs were REP 2004, REP 2006, REP 2107 and REP 2031 (SEQ ID NO:4), these are the unlabeled versions of those ONs described in Example 1. These ONs at various concentrations (in 500 µl of normal saline) were added to 5 ml of fresh whole human blood collected in citrated tubes. The prothrombin time (an accepted measure for the coagulation status of blood) in the presence of these ONs was assessed using accepted clinical laboratory methodologies and compared to the prothrombin time in the presence of equal volumes of normal saline. The relative effect on coagulation was expressed as a ratio ($PTT_{oligo}$:$PTT_{normal\ saline}$) and reported as the normalized ratio (NR). A NR of 1 indicates normal coagulation status and an NR greater than 1 indicated blood that is anti-coagulated. The results of these experiments are illustrated in FIG. 27. For all ONs assessed, there was a dose dependent increase in anti-coagulation.

Figure 28:
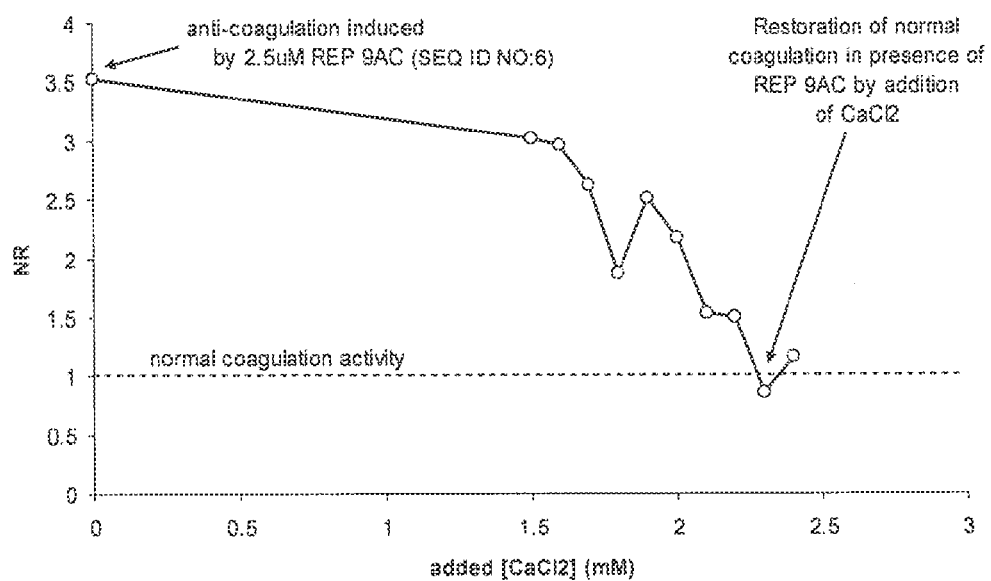
FIG. 28 shows the suppression of the anti-coagulation effect of oligonucleotides by the addition of $CaCl_2$. REP 2055 (a 40mer phosphorothioate with the sequence $(AC)_{20}$; SEQ ID NO:6) was added to blood at 2.5 mM, a concentration which induces significant blood anti-coagulation. REP 2055 was combined with various combinations of $CaCl_2$ and the effects of each concentration of $CaCl_2$ added were determined using accepted clinical laboratory test methodologies. Blood anti-coagulation in the presence of these compounds was monitored by measuring pro-thrombin time (PTT) and comparing it to PTT in the presence of normal saline in the blood using accepted test methodologies. The ratio of PTT in the presence and absence of drug yields the normalized ratio (NR). A NR of 1 indicates normal blood coagulation activity and a NR above 1 indicates blood coagulation activity has been impaired (anti-coagulation).

REP 2055 (SEQ ID NO:6) is a 40mer phosphorothioated ON with sequence $(AC)_{20}$. The effect of addition of 2.5 mM of the sodium salt of REP 2055 on blood coagulation status was assessed as described above. To determine if the anti-coagulation effect was due to chelation of calcium from the blood, the effect of various amounts of calcium supplementation (in the form of calcium chloride) on the REP 2055 (SEQ ID NO:6)-induced anti-coagulation was observed. The results of this experiment are illustrated in FIG. 28. As expected from the results in FIG. 27, 2.5 mM REP 2055 (SEQ ID NO:6) induced a pronounced anti-coagulation of blood. This anti-coagulation was effectively suppressed by supplementation of calcium and could be completely reversed at calcium chloride concentrations greater than 2.25 mM. These results strongly suggest that the anti-coagulation effect of oligonucleotides is mediated by the formation of ON chelate complexes in the blood after ON administration resulting in calcium chelation as described in the above examples. Moreover, these results further identify a method for preventing the anti-coagulation of blood by ONs which is to neutralize the chelating effect of the ON to be administered by preparing the ON as calcium chelate complex. The neutralization of calcium chelation may also be achieved with an ON chelate complex prepared using salts of another divalent metal including but not limited to: magnesium, manganese, iron (2+), copper, and/or zinc. These methods of suppressing oligonucleotide-mediated anti-coagulation can be expected to be effective with oligonucleotides administered to a human or non-human subject by IV or other routes of administration.

The results of this experiment also call into question the nature of the interaction of ONs with serum proteins. Previous assumptions of the nature of ON anticoagulation was that ONs interact directly with proteins of the coagulation cascade but we note that the majority of these proteins are calcium binding proteins or proteins involved in the calcium dependent coagulation cascade (Sheerhan and Lan, 1998, Blood 92: 1617). The fact that the anti-coagulation of blood of ONs can be neutralized by adding calcium and the fact that ONs act as calcium chelaters suggest the following:

The ON protein binding involved in anticoagulation may be necessary but not sufficient for anticoagulation—the removal of calcium from calcium dependent proteins via its chelation by ONs may be the mechanism by which ONs exert anticoagulation activity.

ON protein interactions with components of the coagulation cascade may themselves be calcium dependent.

Albumin, a major blood protein, also binds calcium and is a part of the serum calcium regulatory mechanism. Albumin is also known to interact with ONs and likely plays a major role in the circulating ½ life of ONs in the blood. From the results of the anticoagulation experiment above, it appears that the bulk of protein interactions in the blood may be catalyzed in large part by the calcium chelating functionality of ONs. Therefore in order to reduce serum protein interaction which is also likely to have the effect of reducing the circulating ½ life of ONs and improving their tolerability with parenteral administration, ONs could be administered to a subject as ON chelate complexes. These complexes could be prepared from calcium salts but may also be prepared from other appropriate metal salts so as to neutralize the propensity for ONs to chelate calcium when administered. Such complexes would already have their chelation activity neutralized and would thus be expected to have significantly reduced interaction with serum proteins. The advantages of this reduced serum protein interaction would be the improved tolerability of the administered ON (as a chelate complex) and a shorter ½ life of free ON in the blood.

EXAMPLE IX

Figure 29A:
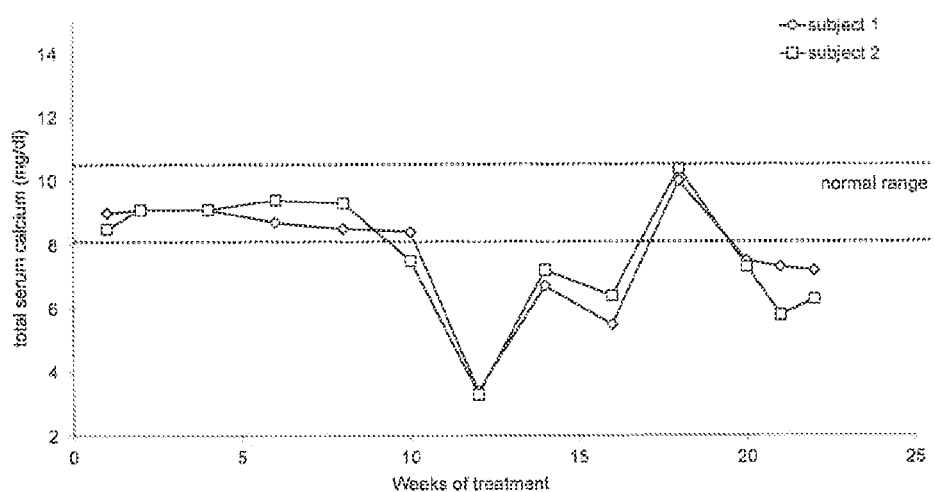
FIG. 29 shows the calcium chelation effect of chronic ON treatment on total serum calcium in patients with chronic liver disease. Patients receiving no mineral supplementation are shown in FIG. 29(A) and patients receiving supplementation while undergoing ON treatment as shown in FIG. 29(B).
Figure 29B:
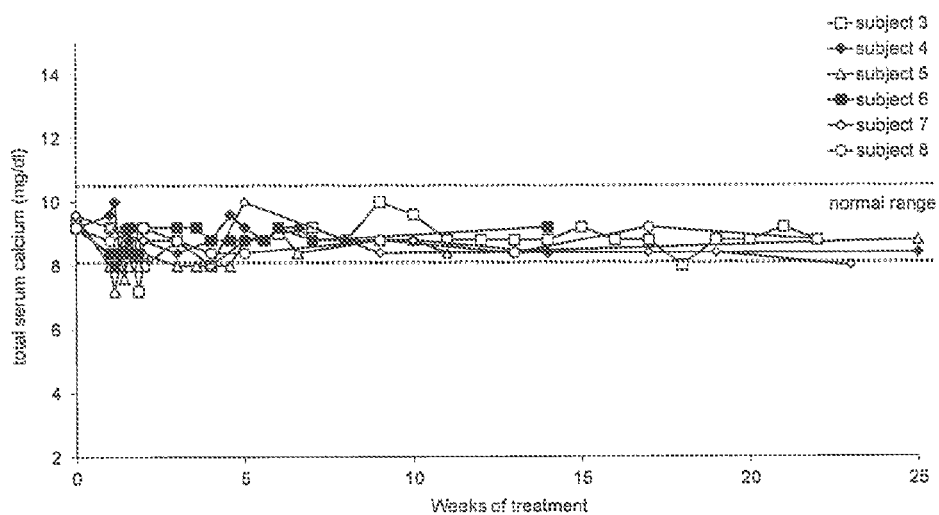

Development of and Prevention of Hypocalcemia in Human Subjects with Chronic ON Treatment To further examine if the chelation of divalent metal cations by ONs described in the above examples has biological relevance in human subjects, the effect of chronic ON administration on serum calcium was examined in patients with chronic liver disease. These subjects are particularly well suited to examine the biological effect (if any) of ON chelation as they have been shown to suffer from vitamin D deficiency which is typically accompanied by mineral metabolism disorders and lowered bone mineral density (Arteh et al., 2010, Dig. Dis. Sci., 55: 2624-2628 and George et al., 2009 World J. Gasteroenterol., 15: 3516-3522). Thus, if the chelation effect of chronically administered ONs was altering divalent metal homeostasis in human subjects (such as calcium) the effect of this alteration would be most easily observed in these patients as they would be poorly able to counteract any serum metal imbalance if it occurred. Patients with chronic hepatitis B infection (with diagnosed chronic liver disease) were treated once weekly with the ON REP 2055 (SEQ ID NO:6) (as a GMP grade sodium salt) by slow IV infusion in normal saline. Total serum calcium levels were monitored in subjects by accepted clinical laboratory methods. The first two subjects receiving ON treatment developed significant hypocalcaemia within 12 weeks of treatment (FIG. 29A). This hypocalcaemia varied in its severity but persisted during the following 13 weeks of treatment. Subsequent subjects receiving chronic ON treatment with REP 2055 (SEQ ID NO:6) were given mineral supplements (providing calcium, magnesium and zinc) to counteract the chelation effects of ON treatment. None of the subjects receiving mineral supplements developed hypocalcaemia while on ON treatment (FIG. 29B). These results demonstrate the chelation activity of ONs does occur in human subjects. This was observed directly with serum calcium but may also be occurring with other biologically relevant divalent metal cations such as magnesium, zinc and copper). Additionally, metal deficiencies caused by ON chelation effects can be corrected by mineral supplementation and may also be reduced by administering ONs as chelate complexes.

As ONs have been shown to chelate divalent metal cations in human subjects, the administration of a non-chelated ONs could be useful for the chelation of harmful heavy metals in a subject such as mercury, cadmium, lead or even chromium (6+). Such a method would involve the administration of a pharmaceutically acceptable ON salt in an appropriate excipient, the ON designed to be devoid of sequence-dependent functionality (such as but not limited to the specific sequence ONs described in Example III) preferably by IV administration but also by other parenteral routes. Patients with normal liver function would be expected to be able to counteract the calcium chelation which would occur however mineral supplementation could be provided (as in Example IX) to ensure that serum depletion of biologically important divalent cations would be prevented. Such unchelated ONs would sequester heavy metals present in the blood, immediately reducing or eliminating the harmful effects of these metals and also potentially accelerate their elimination from the subject in questions.

Since it has been also demonstrated that double stranded ONs can also form ON chelate complexes (and therefore also sequester divalent metals), it is expected that the administration of any double stranded nucleic acid (for example an siRNA) would also be expect to have at least some of the chelation effects described for singe stranded ONs in the example above. Therefore, it may be advantageous to prepare double stranded ONs as chelate complexes prior to administration.

EXAMPLE X

ON Chelate Complexes can Suppress Injection Site Reactions of Subcutaneously Administered Oligonucleotides Injection site reactions (ISRs) with subcutaneously administered oligonucleotides in human patients are common, even with oligonucleotides highly modified to minimize their immunostimulatory properties. Since subcutaneous administration involves the injection of highly concentrated oligonucleotides (typically >100 mg/ml), the chelation effect (most likely of calcium but may be also other divalent metals such as magnesium) localized around the injection site must be substantial and could contribute to the ISRs routinely observed. To test this hypothesis, REP 2055 (SEQ ID NO:6) or REP 2139 (SEQ ID NO: 13, a REP 2055 analog having all riboses 2' O methylated and all cytosine bases 5' methylated) was administered by subcutaneous administration to human patients. Both solutions were prepared aseptically in normal saline, either as a sodium salt or as a calcium chelate complex (see Tables 7 and 8 and according to the procedure in Example VIII). To control for patient to patient variation, both formulations of each ON were assessed for injection reactivity in the same human subject. Subjects were monitored for ISRs at each injection site for 12 hours following REP 2055 (SEQ ID NO:6) administration and for 72 hours following REP 2139 (SEQ ID NO:13) administration. The results of this experiment are presented in Table 7 and 8.

TABLE 7

Suppression of injection site reactivity of REP 2055 (SEQ ID NO: 6) by its preparation as a calcium chelate complex (1 cc bolus injection, 20 mg CaCl$_2$/100 mg ON)

| Human subject | Injection site reaction 25 mg REP 2055 (SEQ ID NO: 6); 12 hours after injection) | | |
|---|---|---|---|
| | 25 mg REP 2055 (sodium salt) | 25 mg REP 2055 (Ca chelate) | 100 mg REP 2055 (Ca chelate) |
| 1 | Induration: +++ inflammation: +++, tenderness: ++, pain: ++ | Induration: none inflammation: none tenderness: none pain: none | Induration: + inflammation: none tenderness: none pain: none |
| 2 | Induration: +++ inflammation: +++, tenderness: +++, pain: +++ | Not assessed | Induration: + inflammation: ++ tenderness: none pain: none |

TABLE 8

Suppression of injection site reactivity of REP 2139 (SEQ ID NO: 13) by its preparation as a calcium chelate complex (2 cc bolus injection, 30 mg CaCl$_2$/100 mg ON)

| Human Subject | ISR side effect | Injection Site Reaction 100 mg REPREP 2139 (SEQ ID NO: 13) | | | | | |
|---|---|---|---|---|---|---|---|
| | | 24 hours | | 48 hours | | 72 hours | |
| | | Sodium salt | Calcium chelate | Sodium salt | Calcium chelate | Sodium salt | Calcium chelate |
| 1 | Induration | ++ | − | ++ | − | + | − |
| | Inflammation | ++ | + | ++ | − | + | − |
| | Tenderness | + | − | + | − | − | − |
| | Pain | + | − | − | − | − | − |
| 2 | Induration | ++ | + | ++ | +/− | + | − |
| | Inflammation | +++ | + | ++ | +/− | + | − |
| | Tenderness | + | − | +/− | − | − | − |
| | Pain | + | − | +/− | − | +/− | − |

These results demonstrate that the administration of ONs as calcium chelate complexes substantially reduces or eliminates ISRs with two different subcutaneously administered ONs. These results further demonstrate that the chelation of calcium (and potentially other divalent metals) by ONs plays a role in the manifestation of ISRs typically associated with the subcutaneous administration of ONs. Furthermore, these results identify a method for the prevention of ISRs with any subcutaneously administered ON by performing the administration of said ON as chelate complex. In these examples, calcium was used as the vehicle for the formation chelate complexes but the mitigation of ISRs would also be expected to occur with ON chelate complexes that had been prepared with another appropriate divalent metal other than calcium. Any ON metal chelate complex would be expected to have its propensity for chelating calcium neutralized which would be the underlying mechanism for the improved SC tolerability of the ON when administered as a chelate complex. The ability of ON chelate complexes to suppress oligonucleotide-induced ISRs is expected to be effective for any ON of any specific sequence and or modification or single or double stranded ONs in light of the broadly conserved nature of ON chelate complex formation disclosed in the examples herein. Using calcium as the exemplary divalent metal in this example, other calcium salts could be used in the preparation of ON chelate complexes and be expected to yield ON chelate complexes having the same suppressive effects on oligonucleotide-mediated ISRs with subcutaneous administration including but not restricted to calcium gluconate, calcium citrate, calcium lactate, calcium malate, calcium aspartate, calcium fumarate, calcium ascorbate, calcium benzoate, calcium erythorbate, and/or calcium propionate. ON chelate complexes could be prepared with salts of other divalent metal cations such as but not limited to: magnesium, manganese, iron, copper, zinc.

In the preparation of ON chelate complexes, it may be desirable to use other cations which are not divalent atoms but which can similarly prevent the chelation effect of oligonucleotides. ON chelate complexes prepared with these cations could also be used in formulations to suppress anticoagulation by ONs or to suppress injection site reactions with ON when administered subcutaneously or to prevent the sequestration of biologically important divalent metals after ON administration. Such counter ions may include without restriction: atoms of a 3+ or greater charge state or organic cations.

In the preparation of ON chelate complexes, it may be preferable to prepare ON chelates using a mixture of divalent cations (i.e. with calcium and magnesium salts). Such mixed ON chelates may be easier to manufacture and have greater solubility than chelates prepared with a single divalent cation and thus would be better suited for high concentration applications.

Given the examples above using diverse ON sequences, with diverse modifications and in the single stranded or double stranded state and using diverse divalent metals, the formation of ON chelation complexes can be considered to be a universal feature of any and all ONs which have a phosphodiester backbone (whether phosphorothioated or not), regardless of other modifications. As such, the formation of ON chelate complexes in the blood or the subcutaneous space is a normal feature any ON administration when ONs are administered as salts (typically sodium salts), resulting in the sequestration of divalent metal cations even though the secondary effects of this chelation may be asymptomatic in the specific subject population receiving the ON in question. Importantly, there are several examples of ONs (PRO-051/ GSK2402968—Goemans et al., 2011 New England J. Med., 364: 1513-1522 and ISIS 301012 (mipomersen)—Viser et al., 2010, Curr. Opin. Lipidol. 21: 319-323) which have clearly shown the ISR reactions with subcutaneous administration (as sodium salts) which are similar to the ISRs observed in Example IX and are thus diagnostic of ON chelate complex formation following administration. Even though both of these ONs have different sequences and different 2' ribose modifications, they both have a phosphodiester backbone (in both cases phosphorothioated) and so can form ON chelate complexes and sequester divalent metals from the local environment (in this case the subcutaneous space). Moreover, both of these ONs have been shown to be able to exert their biological effects even though ON chelation must be occurring, therefore ON chelate complexes in biological systems do not interfere with the biological activity of ONs.

It is widely accepted and well demonstrated in the art that all phosphorothioated ONs (irrespective of nucleotide sequence) typically achieve the highest drug concentrations in the kidney and the liver. Historically, chronic administration of many different phosphorothioated ONs have been associated with mild liver or kidney dysfunction. While the cause of these dysfunctions has not been clearly elucidated, given the conserved chelation effects of ONs in general, it is likely that the chelation of divalent metals in the liver and kidney is significant with chronic ON administration because the chelation activity may be most pronounced in these organs due to the high concentrations of ONs present. Administration of ONs as chelate complexes will not alter organ biodistribution (or affect bioactivity as shown above) but may serve to prevent the metal deficiencies in the liver and kidney that are having an impact on the normal function of these organs.

Given that ON chelate complexes result in the formation of multimeric ON complexes in solution, these complexes are likely to have a much greater resistance to nuclease degradation and potentially to hydrolysis and phosphorothioate ONs may also be more resistant to oxidation. Therefore, the storage of any ON as a chelate complex may greatly increase its stability in aqueous solution without significantly altering its bioactivity when administered to a subject.

What is claimed is:

1. A method for suppressing or reducing the anticoagulation effect of an oligonucleotide administration to a subject; for suppressing or reducing subcutaneous injection site reactions of the oligonucleotide administration to the subject; or for improving the tolerability of the oligonucleotide when administered by IV infusion in the subject, said method comprising the step of administering said oligonucleotide to the subject as a chelate complex, said chelate complex comprising at least two oligonucleotides linked intermolecularly by a divalent cation.

2. The method of claim 1, wherein said chelate complex is a calcium chelate complex.

3. The method of claim 1, wherein said chelate complex is a magnesium chelate complex.

4. The method of claim 1, wherein said chelate complex is a mixed magnesium/calcium chelate complex.

5. The method of claim 1, wherein said chelate complex comprises at least one double stranded oligonucleotide.

6. The method of claim 1, wherein said chelate complex comprises at least one oligonucleotide comprising at least one phosphorothioate linkage.

7. The method of claim 1, wherein said chelate complex comprises at least one oligonucleotide fully phosphorothioated.

8. The method of claim 1, wherein said chelate complex comprises at least one oligonucleotide with one 2' modified ribose.

9. The method of claim 1, wherein said chelate complex comprises at least one oligonucleotide which has each ribose 2' O-methylated.

10. The method of claim 1, wherein said chelate complex comprises at least one oligonucleotide consisting of SEQ ID NOs: 3 to 14.

11. The method of claim 1 wherein said chelate complex comprises at least one oligonucleotide comprising at least one 5-methylcytosine.

12. The method of claim 1, wherein said chelate complex comprises at least one oligonucleotide consisting of SEQ ID NO: 6 further comprising at least one 5-methylcytosine.

13. The method of claim 1, wherein said chelate complex comprises at least one oligonucleotide consisting of SEQ ID NOs: 3 to 12 wherein each cytosine is 5-methylcytosine.

14. The method of claim 1, wherein said chelate complex further comprises a pharmaceutically acceptable excipient.

* * * * *